US012583884B2

(12) United States Patent
Piazza et al.

(10) Patent No.: US 12,583,884 B2
(45) Date of Patent: Mar. 24, 2026

(54) 3BETA-(BENZYLOXY)-17ALPHA-METHYL-PREGN-5-EN-20-ONE FOR USE IN THE TREATMENT OF COGNITIVE DISORDERS

(71) Applicants: AELIS FARMA, Bordeaux (FR); UNIVERSITE DE BORDEAUX, Bordeaux (FR); INSERM (INSTITUT NATIONAL DE LA SANTÉ ET DE LA RECHERCHE MÉDICALE), Paris (FR)

(72) Inventors: Pier Vincenzo Piazza, Bordeaux (FR); Sandy Fabre, Bordeaux (FR); Stéphanie Monlezun, Bordeaux (FR); Mathilde Metna, Bordeaux (FR); Monique Vallee, Bordeaux (FR); Jean-Michel Revest, Bordeaux (FR); Daniela Cota, Bordeaux (FR); Giovanni Marsicano, Bordeaux (FR); Aline Marighetto, Bordeaux (FR); Andrés Ozaita, Barcelona (ES); Rafael Maldonado, Barcelona (ES)

(73) Assignees: AELIS FARMA, Bordeaux (FR); UNIVERSITE DE BORDEAUX, Bordeaux (FR)

( * ) Notice: Subject to any disclaimer, the term of this patent is extended or adjusted under 35 U.S.C. 154(b) by 903 days.

(21) Appl. No.: 17/414,826

(22) PCT Filed: Dec. 18, 2019

(86) PCT No.: PCT/EP2019/085927

§ 371 (c)(1),
(2) Date: Jun. 16, 2021

(87) PCT Pub. No.: WO2020/127468

PCT Pub. Date: Jun. 25, 2020

(65) Prior Publication Data

US 2022/0017562 A1 Jan. 20, 2022

(30) Foreign Application Priority Data

Dec. 18, 2018 (EP) .................................... 18306716

(51) Int. Cl.
*C07J 7/00* (2006.01)
*A61K 31/57* (2006.01)
(Continued)

(52) U.S. Cl.
CPC ............... *C07J 7/009* (2013.01); *A61P 25/28* (2018.01)

(58) Field of Classification Search
CPC ........... C07J 7/009; A61P 25/28; A61P 25/16; A61K 31/57; A61K 31/573
See application file for complete search history.

(56) References Cited

U.S. PATENT DOCUMENTS 10,040,816 B2 * 8/2018 Piazza ........................ A61P 9/04
10,150,793 B2 12/2018 Piazza et al.
(Continued)

FOREIGN PATENT DOCUMENTS

CN 101506172 A 8/2009
CN 105189529 A 12/2015
(Continued)

OTHER PUBLICATIONS

Annus et al, The Down syndrome brain in the presence and absence of fibrillar Î$^2$-amyloidosis, Neurobiol. Aging, 53, pp. 11-19 (Year: 2019).*
(Continued)

*Primary Examiner* — Jeffrey S Lundgren
*Assistant Examiner* — Alexander K. Showalter
(74) *Attorney, Agent, or Firm* — Hogan Lovells US LLP

(57) ABSTRACT

The present invention generally relates to a specific pregnenolone derivative for its use for the treatment of a cog-
(Continued)

nitive disorders. More particularly, the invention relates to a compound of Formula (I)

Formula (I)

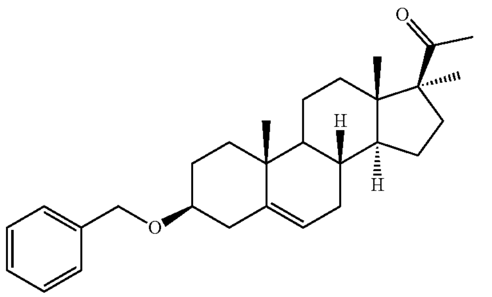

for its use in the treatment of cognitive disorders. Indeed, the compound of the invention is in vivo very potent in correcting the cognitive impairments observed in cognitive disorders.

12 Claims, 10 Drawing Sheets

(51) Int. Cl.

| | |
|---|---|
| ***A61K 31/573*** | (2006.01) |
| ***A61P 25/16*** | (2006.01) |
| ***A61P 25/28*** | (2006.01) |

(56) References Cited

U.S. PATENT DOCUMENTS

| | | | | |
|---|---|---|---|---|
| 10,259,839 | B2 | 4/2019 | Piazza et al. | |
| 11,484,537 | B2 | 11/2022 | Piazza et al. | |
| 2007/0054891 | A1 | 3/2007 | Davidson | |
| 2014/0200200 | A1 | 7/2014 | Piazza et al. | |
| 2016/0067235 | A1* | 3/2016 | Ozaita Mintegui .. | A61K 31/352<br>514/210.01 |
| 2016/0145294 | A1 | 5/2016 | Piazza | |
| 2021/0030768 | A1 | 2/2021 | Piazza et al. | |
| 2022/0153776 | A1 | 5/2022 | Piazza et al. | |
| 2023/0226076 | A1 | 7/2023 | Piazza et al. | |

FOREIGN PATENT DOCUMENTS

| | | | |
|---|---|---|---|
| WO | 2008010073 | A1 | 1/2008 |
| WO | 2012160006 | A1 | 11/2012 |
| WO | 2014083068 | A1 | 6/2014 |

OTHER PUBLICATIONS

Boat et al. (ed), âClinical Characteristics of Intellectual Disabilitiesâ, Ch. 9 of Mental Disorders and Disabilities Among Low-Income Children, National Academies Press (US) (p. 173 only) (Year: 2015).*

Glatt et al., âls Schizophrenia A Neurodevelopmental Disorder?â, Ch. 9 of Schizophrenia, Oxford (Abstract only) (Year: 2019).*

Morris-Rosendahl et al., Neurodevelopmental disordersathe history and future of a diagnostic concept, Dialog. Clin. Neurosci., 22, pp. 65-72 (Year: 2020).*

Murray et al., Is schizophrenia a neurodevelopmental disorder?, Brit. Med. J., 295, p. 681-682 (Year: 1987).*

Spitzer et al., Medical and mental disorder: Proposed definition and criteria, Ann. Med. Psychol., rev. psychiatr. (Paris), 176, pp. 656-665 (Year: 2018).*

Tsuang, Schizophrenia: genes and environment, Biol. Psych., 47, pp. 210-220 (Year: 2000).*

Nair, A simple practice guide for dose conversion between animals and human, J. Basic. Clin. Pharm., 7, pp. 27-31 (Year: 2016).*

Marx, C. E. et al, "Proof-of-concept trial with the neurosteroid pregnenolone targeting cognitive and negative symptoms in schizophrenia" Neuropsychopharmacology (2009) 34(8):1885-1903.

International Search Report and Written Opinion for PCT/EP2019/085927, mailed on Mar. 18, 2020.

Breton, M.C. et al., "Traitement pharmacologique de la maladie d'Alzheimer et des maladies apparentées: rapport d'évaluation des technologies de la santé"; (2015); Institut national d'excellence en santé et en services sociaux, 89 Pages.

"Rapport d'évaluation des médicaments indiqués dans le traitement symptomatique de la maladie d'Alzheimer" (2016); Commission de la Transparence. Haute Autorité de Santé.

Beyer, C.E. et al. "Depression-like phenotype following chronic CB1 receptor antagonism", (2010), Neurobiology of Disease 39, 148-155.

Hunter J. et al., "Epidemiology of Fragile X Syndrome: A Systematic Review and Meta-Analysis", (2014), American Journal Medical Genetics 164A, 1648-1658.

Kishnani, P.S. et al., "Donepezil for treatment of cognitive dysfunction in children with Down syndrome aged 10-17", (2010), Journal Medical Genetics A, 152A, 3028-3035.

Kumin L. et al.; Employment in Adults with Down Syndrome in the United States: Results from a National Survey, (2016), Journal of Applied Research in Intellectual Disabilities 29, 330-345.

Marighetto, A. et al., "Studying the impact of aging on memory systems: contribution of two behavioral models in the mouse", (2012), Current Topics in Behavioral Neuroscience10, 67-89.

Moreira, F.A. et al., "Central side-effects of therapies based on CB1 cannabinoid receptor agonists and antagonists: focus on anxiety and depression", (2009), Best Practice & Research Clinical Endocrinology & Metabolism 23, 133-144.

Overstreet, D.H., "Modeling Depression in Animal Models", (2021), Methods in Molecular Biology, 829, 125-144.

Rinaldi-Carmona, M. et al., "Characterization of Two Cloned Human CB1 Cannabinoid Receptor Isoforms", (1996), Journal Pharmacology Experimental Therapeutics, 278, 871-878.

Varni, J.W. et al., "PedsQL 4.0: reliability and validity of the Pediatric Quality of Life Inventory version 4.0 generic core scales in healthy and patient populations", (2001), Medical Care 39, 800-812.

Zavatti, M. et al., "Effects of the cannabinoid antagonist SR 141716 on sexual and motor behaviour in receptive female rats", (2011), Clinical and Experimental Pharmacology and Physiology, 38, 771-775.

"Donepezil, galantamine, rivastigmine and memantine for the treatment of Alzheimer's disease", (2011), Technology appraisal guidance, 76 pages.

Kharkevich, D.A., Pharmacology, 10th ed. M.: GEOTAR-Media, 2010, p. 73-74.

Zakharov, V.V., et al. "Cognitive disorders in the elderly and senile age", a manual for doctors, Moscow, 2005, p. 9, 17, 60.

Zhulenko V.N., et al., G.I. Pharmacology. M.: KolosS, 2008, pp. 34-35.

"Diagnostic and statistical manual of mental disorders", DSM-5 (2013), Washington, D.C: American Psychiatric Association). pp. xiii-xxxii, 31-86, 591-643, and 839-896.

Goepp, J. "Enhancing Cognitive Function with Pregnenolone", Life Extension Magazine Nov. 2007, retrieved from the internet at https://www.lifeextension.com/magazine/2007/11/report_pregnenolone (accessed Apr. 19, 2024, at 3:18 PM).

Vallee, M. et al, "Neurosteroids and potential therapeutics: focus on pregnenolone", J. Steroid. Biochem. Mol. Biol. (2015) vol. 160, p. 78-87.

Arnone, M., et al. , "Selective inhibition of sucrose and ethanol intake by SR 141716, an antagonist of central cannabinoid (CB1) receptors", (1997), Psychopharmacology (Berl.) 132, 104-106.

(56) References Cited

OTHER PUBLICATIONS

Bellocchio, L., et al. , "Activation of the sympathetic nervous system mediates hypophagic and anxiety-like effects of CB, receptor blockade", (2013), Proc. Natl. Acad. Sci. U.S.A. 110, 4786-4791.
Beringer, P. ,"Remington: the science and practice of pharmacy", (2011), (Philadelphia; London: Lippincott Williams & Wilkins).
Berry-Kravis, E., et al. "Outcome Measures for Clinical Trials in Fragile X Syndrome", (2013) Journal of Developmental & Behavioral Pediatrics 34, 508-522.
Burckhardt, C.S., et al. "The Quality of Life Scale (QOLS): reliability, validity, and utilization", (2003) Health Qual Life Outcomes 1, 60.
Busquets-Garcia, A., et al. "Targeting the endocannabinoid system in the treatment of fragile X syndrome", (2013), Nature Medicine 19, 603-607.
Carai, M.A.M., et al. "Efficacy of rimonabant and other cannabinoid CB1 receptor antagonists in reducing food intake and body weight: preclinical and clinical data", (2006), CNS Drug Rev 12, 91-99.
Chang, K.T., et al. "Meeting at the crossroads: common mechanisms in Fragile X and Down syndrome", (2013), Trends Neurosci. 36, 685-694.
Edgin, J.O., et al. "Human and mouse model cognitive phenotypes in Down syndrome: implications for assessment", (2012), Prog. Brain Res. 197, 123-151.
Ennaceur, A. "One-trial object recognition in rats and mice: methodological and theoretical issues", (2010), Behav. Brain Res. 215, 244-254.
Esbensen, A.J., et al. "Outcome Measures for Clinical Trials in Down Syndrome. American Journal on Intellectual and Developmental Disabilities", (2017), 122, 247-281.
Etchamendy, N., et al. "Evidence for a virtual human analog of a rodent relational memory task: A study of aging and MRI in young adults", (2012), Hippocampus 22, 869-880.
Gardiner, K.J. "Pharmacological approaches to improving cognitive function in Down syndrome: current status and considerations", (2015), Drug Des Devel Ther 9, 103-125.
Grieco, J., et al. , "Down syndrome: Cognitive and behavioral functioning across the lifespan", (2015), American Journal of Medical Genetics Part C: Seminars in Medical Genetics 169, 135-149.
Hanney, M., et al. "Memantine for dementia in adults older than 40 years with Down's syndrome (Meadows): a randomised, double-blind, placebo-controlled trial", (2012), The Lancet 379, 528-536.
Hessl, D., et al. "The NIH Toolbox Cognitive Battery for intellectual disabilities: three preliminary studies and future directions", (2016), Journal of Neurodevelopmental Disorders 8.
Kazdoba, T.M., et al. "Modeling fragile X syndrome in the Fmr1 knockout mouse" (2014), Intractable Rare Dis Res 3, 118-133.
Laprairie, R.B., et al. "Type 1 cannabinoid receptor ligands display functional selectivity in a cell culture model of striatal medium spiny projection neurons", (2014) J. Biol. Chem. 289, 24845-24862.
Patel, S., et al. "Pharmacological evaluation of cannabinoid receptor ligands in a mouse model of anxiety: further evidence for an anxiolytic role for endogenous cannabinoid signaling", (2006). J. Pharmacol. Exp. Ther. 318, 304-311.
Seely, K.A., et al, "AM-251 and rimonabant act as direct antagonists at mu-opioid receptors: Implications for opioid/cannabinoid interaction studies" (2012), Neuropharmacology 63, 905-915.
Bellami, A., et al., "Temporal binding function of dorsal CA1 is critical for declarative memory formation", (2017), Proc. Natl. Acad. Sci. U.S.A. 114, 10262-10267.
Sheehan, B. "Assessment scales in dementia", (2012) Ther Adv Neurol Disord 5, 349-358.
Shore, D.M., et al. "Allosteric Modulation of a Cannabinoid G Protein-coupled Receptor: Binding Site Elucidation and Relationship to G Protein Signaling", (2014), Journal of Biological Chemistry 289, 5828-5845.
Vallee, M., et al. , "Pregnenolone can protect the brain from cannabis intoxication", (2014), Science 343, 94-98.
Walf, A.A., et al. "The use of the elevated plus maze as an assay of anxiety-related behavior in rodents" (2007), Nat Protoc 2, 322-328.
"Donepezil, galantamine, rivastigmine and memantine for the treatment of Alzheimer's disease" (2011), Technology appraisal guidance. National Institute for Health and Care Excellence.
EPAR discussion. https://www.ema.europa.eu/documents/scientific-discussion/acomplia-epar-scientific-discussion_en.pdf, (2006).

* cited by examiner

Route C

Pregnenolone
Formula (III)
Formula (IV)
Formula (V)
Formula (I)

Route D

Pregnenolone
Formula (V)
Formula (I)

3BETA-(BENZYLOXY)-17ALPHA-METHYL-PREGN-5-EN-20-ONE FOR USE IN THE TREATMENT OF COGNITIVE DISORDERS

RELATED APPLICATIONS

This application is a U.S. National Stage application under 35 U.S.C. 371 of PCT/EP2019/085927, having an international filing date of Dec. 18, 2019, which designated the United States, which PCT application claims the benefit of European Application No. 18306716.4 filed on Dec. 18, 2018, each of which are incorporated herein by reference in their entireties.

FIELD OF THE INVENTION

The present invention relates to the field of mental disorders, and in particular, to the field of cognitive disorders. It relates to a particular pregnenolone derivative, "3β-(benzyloxy)-17α-methyl-pregn-5-en-20-one" (3Bn17MeP), that cannot be metabolized into active pregnenolone metabolites and its use for the treatment of cognitive disorders.

BACKGROUND OF THE INVENTION

Cognitive disorders are defined as disorders resulting in impairments of the cognitive function of an individual that renders independent living in society difficult or impossible without treatment.

Cognitive disorders relate to impairments in any domains of the cognitive functioning including learning and memory (e.g. short- and long-term memories, acquisition, consolidation, recall and recognition of memory), executive functions (e.g. working memory, cognitive flexibility, decision-making), complex attention, language, perceptual-motor abilities or social cognition. Cognitive functions are necessary for the global functioning of individuals. Therefore, cognitive disorders affect personal, academic or professional social achievements, with as ultimate consequence a loss of autonomy.

Cognitive disorders can be caused by very heterogenous diseases and can manifest at any life stage. For instance, cognitive disorders can be the consequence of a genetic birth defect, a physical brain injury, a neurodegenerative disease or of cognitive decline associated with ageing.

According to the Fifth Edition of the Diagnostic and Statistical Manual of Mental Disorders (DSM-5™), cognitive disorders are comprised of two disease categories that are distinguished by developmental and lifespan considerations: neurodevelopmental disorders and neurocognitive disorders.

Neurodevelopmental disorders are a group of mental disorders that manifest during the early developmental period (i.e. before entry to elementary school). Typically, neurodevelopmental disorders can be caused by genetic birth defects (e.g. Down syndrome, Fragile X syndrome), developmental anomalies (e.g. brain malformation), maternal diseases (e.g. placental disease) or perinatal environmental factors (e.g. foetal exposure to alcohol). Neurodevelopmental disorders are characterized by intellectual disabilities, adaptative and communication impairments. The consequences for the individuals with neurodevelopmental disorders vary according to the severity of the cognitive impairments, but always impede personal, social and academic activities. For instance, in Down syndrome which is the most common genetic cause of intellectual disability, cognitive impairments mainly manifest by reduced memory and executive functions (Grieco et al., 2015). Acquisition of language and writing are delayed and mental age in adults does not exceed 8 years-old with an Intellectual Quotient <70. Consequently, individuals with Down syndrome are highly dependent, needing for instance specific and individualized education support and being exposed to high rate of unemployment (e.g. 50% in United States). More than half of the individuals with Down syndrome experience non-adapted behaviors and/or difficulties in making social relationships (Grieco et al., 2015; Kumin and Schoenbrodt, 2016).

Neurodevelopmental disorders are highly prevalent. Intellectual disabilities in themselves affect 1% of the general population with Down syndrome representing 1‰ cases (DSM-5™). However, there is currently no drug approved for the treatment of cognitive impairments induced by neurodevelopmental disorders.

Neurocognitive disorders are a group of mental disorders characterized by core cognitive deficits that represent a decline from a previously attained cognitive level. The etiologies of neurocognitive disorders include neurodegenerative disorders (e.g. Alzheimer disease, frontotemporal lobar degeneration, Parkinson disease), vascular diseases, traumatic brain injuries, substance/medication abuse, Human Immunodeficiency Virus (HIV) infection or prion disease.

Neurocognitive disorders can be considered as mild (also called mild cognitive impairments) or major (also called dementia) according to the impact severity on autonomy of individuals with neurocognitive disorders.

Major neurocognitive disorders lead to incapacities of managing daily activities such as paying bills or keeping compliance with medications without assistance. Individual with mild neurocognitive impairments remain independent at the cost of greater effort and adoption of compensatory strategies (DSM-5™).

Neurocognitive disorders are caused by many diseases, their prevalence in the global population is thus hard to estimate. However, in the older population, major neurocognitive disorders affect up to 2% of the 65 years-old population and 30% by 85 years of age. Prevalence of mild neurocognitive disorders reaches 10% at 65 and 25% over the age of 70 (DSM-5™). Frequency of neurocognitive disorders is increasing with the on-going ageing of the global population. Treatments capable of improving cognitive functioning are thus highly awaited.

Pharmacological interventions are currently approved to limit or delay cognitive decline associated with Alzheimer and Parkinson diseases. These are acetylcholinesterase inhibitors (e.g. donepezil, rivastigmine, galantamine) and an inhibitor of the glutamatergic N-methyl-D-aspartate (NMDA) receptors (memantine). Recent examinations of their efficacy and tolerance in patients have been performed in different countries (Haute Autorité de Santé, 2016; National Institute for Health and Care Excellence, 2011; Breton et al., 2015). These studies concluded that these medications have no to weak therapeutic interest due to:

The absence of long-term efficacy in limiting or delaying cognitive loss.

No to modest short-term efficacy in limiting or delaying cognitive loss.

Inefficacy in improving cognitive capacities.

A non-negligible risk of adverse effects; digestive, cardiovascular and neuropsychiatric complications have been reported. The frequency of these adverse events is high, leading up to 30% of treatment interruption (Haute Autorité de Santé, 2016).

In addition, compounds from both pharmacological classes have been tested in patients with neurodevelopmental disorders but have shown no positive therapeutic effects for example in Down syndrome and Fragile X syndrome (Hanney et al., 2012; Kishnani et al., 2010; NCT01120626; NCT00584948, https://clinicaltrials.gov/).

Efficacious and safe pharmacological options are therefore needed for the treatment of cognitive disorders.

The use of compounds (orthosteric antagonists) blocking the activity of the CB1 receptor through inhibition of its orthosteric binding site, the site at which endocannabinoids bind to activate the receptor, has been shown to improve cognitive deficits in Fragile X syndrome (Busquets-Garcia et al., 2013). One of these compounds, rimonabant, was brought to market with the brand name Acomplia®. Unfortunately, available orthosteric antagonists such as rimonabant inhibit the entire activity of the receptor and can also act as inverse agonists of the CB1 receptor, i.e. they not only inhibit the activation of the CB1, but also induce opposite signaling responses of the receptor. Because of this inverse agonist action and the total inhibition of the receptor activity, available methods based on the administration of orthosteric CB1 antagonists also have a series of serious adverse effects. Due to these adverse effects, Acomplia®'s commercialization has been suspended and the development of other methods for inhibiting the orthosteric site of the CB1stopped.

Orthosteric CB1 antagonists and in particular Acomplia® have the following known adverse effects that make them unpractical tools to treat cognitive disorders:

1. They reduce food intake which indicates a general disruption of the reward system;
2. They induce anxiety-related behaviors in animals and anxiety in humans;
3. They induce depression-related behaviors in animals and depression in humans;
4. They induce convulsions and a general behavioral and clinical impairment in safety pharmacology and toxicology studies;
5. They have hepatotoxic effects;
6. They have unspecific effects, inhibiting for instance morphine-induced analgesia through a direct interaction with opioids receptors (Seely et al., 2012).

These effects are clearly incompatible with the use of CB1 antagonists as a therapy of cognitive disorders especially because cognitive disorders affect young and aged populations that are a more fragile and/or weakened population.

It has been recently discovered that when the CB1 receptor is over-activated, the concentration of the steroid hormone pregnenolone increases (3000%) in the brain. Pregnenolone then binds to a specific site on the CB1 receptor, distinct from that bound by CB1 agonists, and acts as an endogenous signaling specific inhibitor of the CB1 receptor (eCB1-SSi). Thus, pregnenolone selectively inhibits CB1-induced activation of the MAPK (Mitogen-Activated Protein Kinase) pathway but not CB1-induced inhibition of Adenylate cyclase. Despite this restricted molecular action, pregnenolone inhibits most of behavioral effects induced by CB1 receptor overactivation in rodents (Vallée et al., 2014).

Unfortunately, pregnenolone cannot be used as a pharmacological treatment because it is poorly available, has a very short half-life and is converted in downstream active steroids.

WO2012/160006 discloses 3β-(benzyloxy)-17α-methyl-pregn-5-en-20-one as derivative of pregnenolone that is not metabolized into downstream steroids and its use for inhibiting CB1 receptor.

Developing a treatment for cognitive disorders based on a signaling-specific inhibition of the CB1 receptor that can be used in humans presents several challenges. Thus, such compound should show concomitantly all the following characteristics:

1. It should improve performances in different domains of the cognitive functioning, considering the variability of cognitive symptoms in patients with cognitive disorders.
2. It should show efficacy in models that approximate human cognitive processes to achieve better translation.
3. It should improve cognitive performances in several diseases/conditions considering the heterogeneity of the etiologies of cognitive disorders.
4. It should be devoid of the known adverse effects of CB1 inhibitors. In particular, it should not induce: a. a decrease in food-intake; b. an increase in anxiety- and depression-related behaviors; c. convulsion and impairments of central nervous system-related clinical signs.
5. It should not modify the binding of other receptors in order to avoid off-target effects or modification of the activity of other therapeutic drugs as in the case of rimonabant.
6. It should not have unspecific behavioral effects including, but not limited to, sedation, excitability, altered spontaneous behavior that can interfere with its therapeutic effects.
7. It should have an acceptable safety margin. It is generally acknowledged that the highest dose inducing no adverse effect should be at least 10 times higher than the therapeutic dose.

For none of the signaling specific inhibitors and other antagonists of the CB1 receptors described in previously available knowledge, all the above-mentioned features have been described. To our knowledge, no compound used to treat cognitive disorders or more generally behavioral disorders has all these characteristics. Thus, the three major classes of psychoactive drugs, anxiolytics, antidepressants and neuroleptics, as well as approved drugs for cognitive deficits associated with Alzheimer disease induce behavioral adverse effects in the range of the therapeutic doses. For example: a. anxiolytic drugs induce sleepiness, decrease alertness and impair memory; b. Antidepressants induce excitability, insomnia and a decrease in libido; c. Neuroleptics induce hormonal disruption, sedation, dyskinesia and involuntary movements. d. acetylcholinesterase inhibitors and memantine induce digestive, cardiovascular and neuropsychiatric adverse effects.

Consequently, a compound that has all the characteristics described in points 1 to 7 would be a major innovation for a drug designed to treat cognitive disorders but also a major innovation for the entire field of psychiatry.

SUMMARY OF THE INVENTION

The present invention generally relates to a specific pregnenolone derivative for its use for the treatment of a cognitive disorder.

More particularly, the invention relates to a compound of Formula (I)

Formula (I)

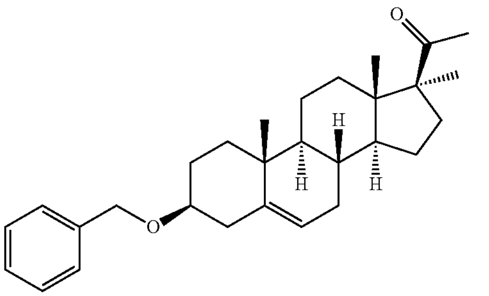

for its use in the treatment of cognitive disorders.

According to the invention, the treatment of cognitive disorders by the compound of Formula (I) comprises:

The complete or partial reversal of the impairment caused by the cognitive disorder including the improvement of the cognitive function.

The prevention of further cognitive decline.

The postponement or the slowing down of cognitive decline or further loss of cognitive abilities.

The present invention is endowed with the following properties:

1. It improves cognitive performances in different cognitive domains (e.g. declarative/relational memory, recognition, executive functions). Therefore, it would be able to meet efficacy criteria on virtually all the profiles of cognitive deficits.
2. It improves performances in cognitive tests that have been successfully employed to detect cognitive impairments both in humans (in a virtual radial maze) and in mice (in a radial maze) using very similar procedures.
3. It improves cognitive performances in different models of diseases/conditions (e.g. Down syndrome, Fragile X syndrome, cognitive deficits associated with aging). Therefore, it would able to meet efficacy criteria on cognitive deficits whatsoever their etiology.
4. It is devoid of the known adverse effects of CB1 inhibitors. It does not induce: a. a decrease in food-intake and in body weight; b. an increase in anxiety- and depression-related behaviors both in healthy and in pathological conditions; c. neurotoxicity, convulsion and impairment of central nervous system-related clinical signs. d. hepatotoxicity and genotoxicity.
5. It does not modify the binding of a large panel of receptors (85) including the opioid receptors.
6. It does not have unspecific behavioral effects including but not limited to sedation, excitability, altered spontaneous behavior that can interfere with its therapeutic effects.
7. It has a very large safety margin (>3500).

This disclosure also relates to a method for treating a cognitive disorder, as described herein, by administering to a subject in need thereof an effective amount of a compound of Formula I. In some examples, the subject in need of therapy has Fragile X, Down syndrome or age-related cognitive decline.

This disclosure also relates to a pharmaceutical composition for treating a cognitive disorder, as described herein, comprising, as an active ingredient, a compound of Formula I. In some examples, the pharmaceutical composition is for treating a subject with Fragile X, Down syndrome or age-related cognitive decline.

BRIEF DESCRIPTION OF THE DRAWINGS

FIG. 5A: Effect of 3Bn17MeP (1; 2.5; 5; 50 and 100 nM) on the THC (1 μM)-induced inhibition of cellular respiration in HEK293 transfected with the wild-type human CB1 receptor. Data are expressed as percentage of THC effect (dotted line at 0% represents the effect of the vehicle of THC; dotted line at 100% represents the effect of THC in absence of 3Bn17MeP). 3Bn17MeP dose-dependently blocks the inhibition of cellular respiration induced by THC with significant effects from 2.5 nM. p<0.001, THC as compared to the vehicle of THC in absence of 3Bn17MeP, Tukey's test. p<0.001, 3Bn17MeP (2.5; 5; 50 and 100 nM) as compared to its vehicle in presence of THC, Tukey's test.

FIG. 5B: Effect of 3Bn17MeP (100 nM) on the THC (1 μM)-induced inhibition of cellular respiration in HEK293 transfected with the wild-type human CB1 receptor (HEK293-hCB1-WT) or with the mutant human CB1 receptor (HEK293-hCB1-Mut) in which the pregnenolone binding site has been invalidated ($hCB1^{p.E1.49G}$; Vallée et al., 2014). 3Bn17MeP inhibits THC (1 μM)-induced decrease in cellular respiration in HEK293 transfected with the hCB1-WT (white-filled bar) whereas 3Bn17MeP does not inhibit this effect of THC in HEK293 transfected with the hCB1-Mut. p<0.01, hCB1-WT as compared to hCB1-Mut in presence of 3Bn17MeP and THC, unpaired t-test).

FIG. 5C: Effect of 3Bn17MeP (0.1; 0.3; 1; 3 and 9 μM) on THC (10 μM)-induced increase in MAPK phosphorylation ($p\text{-Erk1/2}^{MAPK}$). 3Bn17MeP inhibits THC-induced increase in MAPK phosphorylation.

FIG. 5D: Effect of 3Bn17MeP on THC-induced decrease of cAMP levels in CHO cells stably transfected with hCB1. 3Bn17MeP did not modify THC-induced decrease of cAMP. NT, non-treated with THC.

FIG. 6A: 3Bn17MeP restores short-term sequential object recognition of Ts65Dn mice after chronic oral administration (0.6 μg/ml) in drinking water. p<0.01; *p<0.001, $1^{st}$ vs $2^{nd}$ presentation of the same object after a delay of 5 min and ##p<0.01; ###p<0.001, after a delay of 35 min (Fisher's test).

FIG. 6B: 3Bn17MeP restores long-term object recognition of Ts65Dn mice after repeated per os administrations in corn oil (15 μg/kg; b.i.d). ***p<0.001, WT vs Ts65Dn administered with the vehicle of 3Bn17MeP (0 μg/kg) and ###p<0.001, vehicle of 3Bn17MeP (0 μg/kg) vs 3Bn17MeP (15 μg/kg) in Ts65Dn (Tukey's test). No significant difference between WT and Ts65Dn administered with 3Bn17MeP (15 μg/kg, Tukey's test).

FIG. 11A: Effects of acute administration of 3Bn17MeP (0; 0.05; 5; 15 and 30 mg/kg; per os in corn oil) on cumulative food intake of standard chow as measured 3 and 13 hours after light-off. 3Bn17MeP has no effect on food intake.

FIG. 11B: Effects of acute administration of rimonabant (0; 10 mg/kg; ip) on cumulative food intake of standard chow as measured 3 and 13 hours after light-off. Rimonabant decreases food intake. **, p<0.01; rimonabant vs vehicle (0 mg/kg; two-way ANOVA, main treatment effect).

FIG. 11C: Effects of repeated (39 days, once a day) administrations of 3Bn17MeP (0, 0.05; 5; 15 and 30 mg/kg, per os in corn oil) on body weight of mice fed with standard chow. 3Bn17MeP has no effect on body weight.

FIG. 11D: Effects of repeated (39 days, once a day) administrations of rimonabant (0 and 10 mg/kg, ip) on body weight of mice fed with standard chow. Rimonabant decreases body weight.

FIG. 12A: Effects of acute per os administration of 3Bn17MeP in corn oil (30 mg/kg) or vehicle (0 mg/kg) on anxiety-like behaviors as measured by the percentage of time spent and of visits in the open arms of the elevated plus maze. 3Bn17MeP has no effect on anxiety-related behaviors.

FIG. 12B: Effects of acute intraperitoneal administration of rimonabant (10 mg/kg) or vehicle (0 mg/kg) on anxiety-like behaviors as measured by the percentage of time spent and of visits in the open arms of the elevated plus maze. Rimonabant decreases the time spent and the number of visits in open arms. *, p<0.001; , p<0.01; rimonabant vs vehicle (0 mg/kg) (unpaired t-test).

FIG. 12C: Effects of repeated (28 days, once a day) administrations of 3Bn17MeP (0, 0.05; 5; 15 and 30 mg/kg, per os in corn oil) on depression-related behaviors as measured in the sucrose preference test. 3Bn17MeP has no effect on sucrose intake.

FIG. 12D: Effects of repeated (28 days, once a day) administrations of rimonabant (0 and 10 mg/kg; ip) on depression-related behaviors as measured in the sucrose preference test. Rimonabant decreases sucrose intake. *p<0.05, rimonabant vs vehicle (0 mg/kg; unpaired t-test).

FIG. 13A: Effect of 3Bn17MeP, rimonabant (0; 10; 30 and 100 μM) and of the reference positive control staurosporine (100 nM) on toxicity of rat primary cultures of cortical neurons. 3Bn17MeP has no toxic effect in these conditions whereas rimonabant shows dose-dependent toxic effect in these conditions. ***, p<0.001; *, p<0.05, rimonabant vs vehicle (0 μM) (Holm-Sidak test).

FIG. 13B: Effect of 3Bn17MeP (0; 0.1; 0.3; 1; 3; 10; 30 and 100 μM), rimonabant (0; 0.1; 0.3; 1 and 100 μM) and of the reference positive control etoposide (3 μM) on Histone H2AX phosphorylation in HeLa cells. 3Bn17MeP has no effect on phosphorylated H2AX cells whereas rimonabant increased the number of phosphorylated H2AX cells at 100 μM. ***, p<0.001, rimonabant vs vehicle (0 μM) (Holm-Sidak test).

FIG. 14A: Effect of 3Bn17MeP, rimonabant (0; 0.1; 0.3; 1; 3;10; 30 and 100 μM) and of the reference positive control acetaminophen (APAP, 50 mM) on survival of rat primary cultures of hepatocytes. 3Bn17MeP had no hepatotoxic effect whereas rimonabant increased hepatocyte cell death from 3 μM. ***, p<0.001, rimonabant vs vehicle (0 μM) (Holm-Sidak test).

FIG. 14B: Effect of 3Bn17MeP, rimonabant (0; 0.1; 0.3; 1; 3; 10; 30 and 100 μM) and of the reference positive control cyclosporine A (10 μM) on the inhibition of bile canaliculi in rat primary cultures of hepatocytes. 3Bn17MeP had no effect on bile canaliculi whereas rimonabant decreased the number of canaliculi from 1 μM. *, p<0.001; , p<0.01, rimonabant vs vehicle (0 μM) (1-way ANOVA followed by Bonferroni post hoc test).

DETAILED DESCRIPTION

Figure 1:
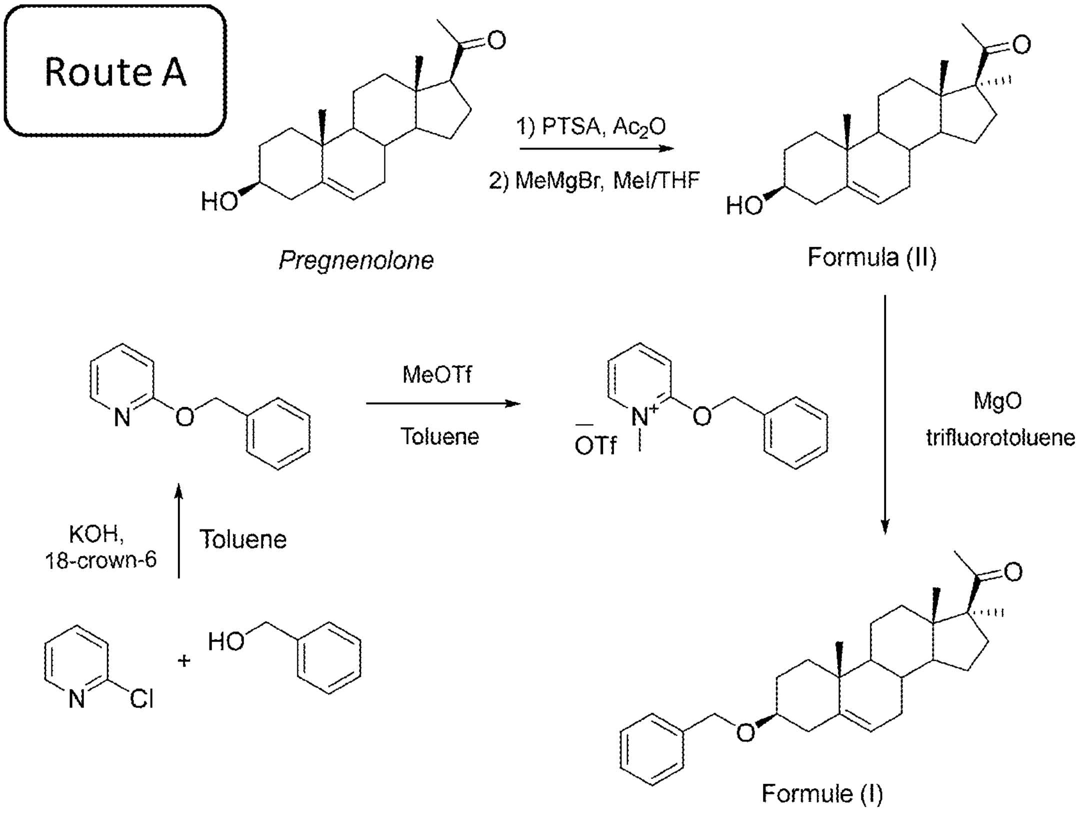
FIG. 1: Flowchart of compound of formula (I) (3Bn17MeP) synthesis following Route A.
Figure 2:
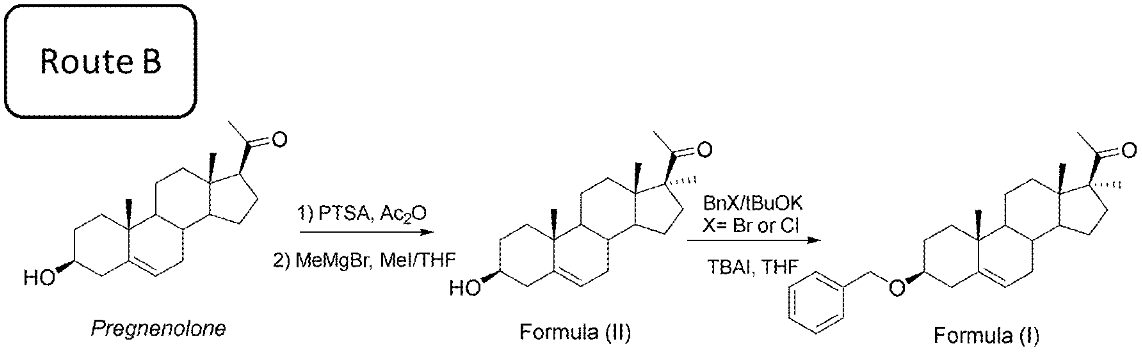
FIG. 2: Flowchart of compound of formula (I) (3Bn17MeP) synthesis following Route B.
Figure 3:
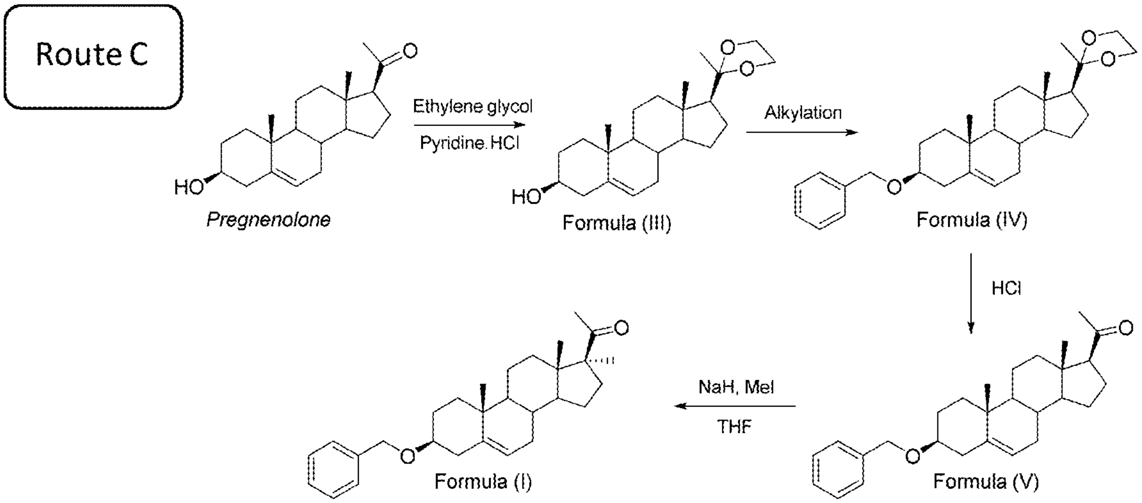
FIG. 3: Flowchart of compound of formula (I) (3Bn17MeP) synthesis following Route C.
Figure 4:
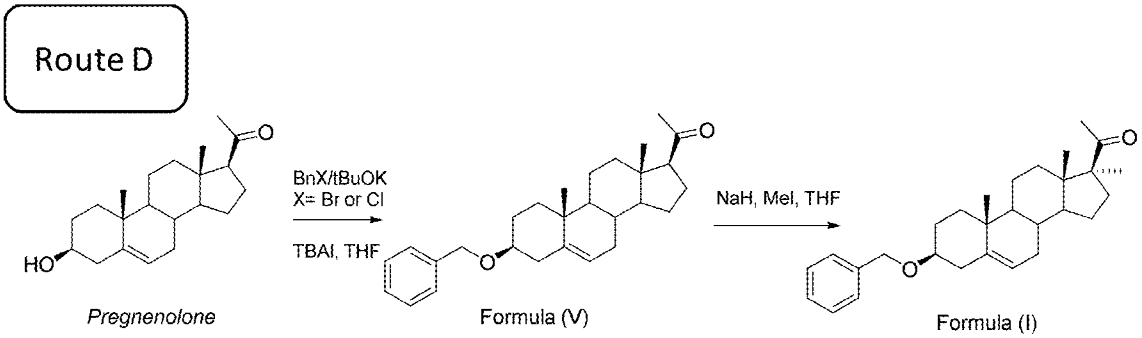
FIG. 4: Flowchart of compound of formula (I) (3Bn17MeP) synthesis following Route D.

The present invention generally relates to a compound of Formula (I):

Formula (I)

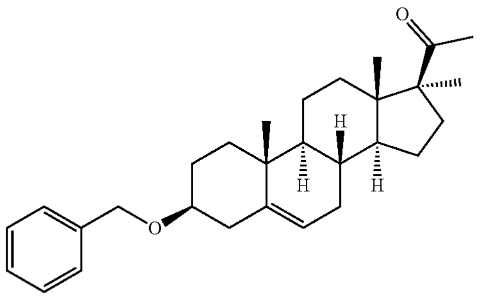

for use in the treatment of a cognitive disorder.

The compound of Formula (I) corrects the cognitive impairments observed in cognitive disorders. In all the cognitive functions and disease models that were evaluated, the administration of 3β-(benzyloxy)-17α-methyl-pregnen-5-en-20-one (3Bn17MeP) fully restores cognitive performances at the levels of healthy controls.

3Bn17MeP shows efficacy in several cognitive domains including long-term memory, recognition and executive functions. The present invention benefits from a wide spectrum of actions on the cognitive function. Therefore, 3Bn17MeP is likely a global cognitive enhancer The compound of the present invention, 3Bn17MeP, does not block the entire activity of the target receptor but only part of its activity. The specific target receptor of the compound of the present invention is the CB1 receptor.

The compound of Formula (I) is thought to reproduce the effects of a newly discovered brain mechanism that provides an endogenous negative feedback, regulating an over activation of the CB1 receptor (Vallée et al., 2014). It is important to note that this regulatory mechanism is triggered only when CB1 is over activated, which is likely to be the case in cognitive disorder, but not when the activation of the receptor is within a more physiological range.

This may explain why the compound of the present invention is extremely potent in correcting cognitive deficits and is thus effective for the treatment of cognitive disorders. Furthermore, due to its signaling-specific action mechanism, the compound of the present invention has no effect on behavior per se in healthy subjects in which CB1 signaling is in the physiological range.

The mechanism of action of the compound of the present invention is in this respect very different from the one of CB1 orthosteric antagonists, which by blocking the binding of endogenous and exogenous agonists of the CB1 receptor, induce a complete inhibition of all CB1 activity and disrupt behavior per se. In addition, the mechanism of action of antagonists does not exist physiologically, i.e. to the best of our knowledge, there are no endogenous compounds, which like antagonists, block the binding of a CB1 agonists to the receptor. Because of the artificial nature of this mechanism of action, these antagonists, in addition to correct for an over-activation of a target receptor, generally lower its activity below basal levels, disrupting physiology and generating side effects.

The different mechanism of action between the compound of the present invention and orthosteric antagonists, such as rimonabant, explains why both drugs can correct cognitive disorders but do not share other behavioral effects.

Hence, the compound of the present invention is not a CB1 orthosteric antagonist and as such does not block all the cellular effects induced by CB1 receptor activation, as the orthosteric CB1 antagonist rimonabant does.

Still advantageously and more generally no adverse effect has been observed with the compound of the present invention.

The lack of adverse effect, and in many cases, the absence of effect of the compound of the present invention in healthy controls are probably due to the specific structure and mechanism of action of the compound of the present invention.

The inventors demonstrate that the compound of the invention has concomitant characteristics that make it a unique ideal tool to treat cognitive disorders. These characteristics include but are not limited to:

1. The compound of the present invention has a unique mechanism of action tailored as an endogenous brain mechanism to overcome an over-activation of the CB1 receptor, but seems to have no effect on the basal activity of the receptor. Disruption of the basal activity of the target system is often responsible for some of the adverse effects of antagonists. In addition, the compound of the present invention is very selective and does not interact with any of the 85 receptors tested. Off-target effects are often responsible for some of the adverse effects of new chemical entities. Cellular activity of the CB1 receptor is then inhibited in a selective and signaling-specific manner.
2. The compound of the present invention shows in vivo a very high potency in correcting a large spectrum of cognitive impairments including long-term memory, recognition and executive functions impairments.
3. The compound of the present invention shows in vivo efficacy in models of different cognitive disorders including Down syndrome, Fragile X syndrome and age-related cognitive decline.
4. The compound of the present invention has none of the adverse effects of orthosteric CB1 antagonists, including but not limited to: a. the decrease in food intake; b. the increase in anxiety- and depression-related behaviors; c. neurotoxicity, induction of clonic convulsion and clinical sign related to an impairment of the central nervous system. d. hepatotoxicity and genotoxicity.
5. The compound of the present invention does not cause unspecific behavioral effects even at doses that are thousands of times higher than the effective dose for the improvement of cognitive functions. These effects include, but are not limited to, changes in spontaneous behaviors, sedation, excitability.
6. The compound of the present invention has no adverse or toxic effects, in vitro and in vivo, at doses thousands of time higher than the effective dose for the improvement of cognitive functions. Consequently, the compound of the present invention presents a high safety index (>3500).

According to the present invention, "cognitive disorders" can be understood as intellectual disorders, cognitive or intellectual impairments, cognitive or intellectual disabilities, mental retardation or cognitive decline and includes all the diseases/conditions that can be associated with cognitive disorders.

Cognition or cognitive function can be defined as all the mental activities dedicated to information processing. They include elementary functions such as perception and motor skills as well as high order processes such as attention, learning and memory, reasoning or executive functions. Deficits in cognition relates to impairment in any cognitive domains including:

Complex attention: sustained attention, divided attention, selective attention and processing speed. For instance, complex attention deficits can lead to difficulties in holding information in mind in environment with distractors or making errors in routine tasks.

Executive functions: planning, decision making, working memory, responding to feedback/error correction, overriding habits/inhibition and mental flexibility. For instance, executive functions deficits can lead to difficulties in completing multistage projects, in planning daily life activities or in following conversations.

Learning and memory: immediate and recent memories including free or cued recall and recognition, long- to very long-term memories and implicit learning. For instance, consequences in learning and memory impairment can be losing tracking on bills payment or repeating self in conversation.

Language: expressive language and comprehension. For instance, language deficit can be associated with the usage of general rather than specific terms, making grammatical errors. Severe forms of language deficits lead to echolalia or mutism.

Perceptual-motor abilities: drawing, praxis (learning of motor sequences) and gnosis (e.g recognition of faces and colors): perceptual-motor deficits can lead to difficulties in achieving previously familiar activities such as using tools or driving.

Social recognition: capacity to recognize emotions expressed by others, and to consider thoughts and intention expressed by others in peculiar situations. Social recognition impairment can lead for instance to decrease empathy, to express behaviors or speeches that are out of accepted social ranges (e.g. inappropriate clothing) or to hold conversations.

In the present case, a cognitive disorder can refer to a pathological condition in which cognitive disturbances are greater than the standard cognitive level for age-matched individuals. Additionally, cognitive disorders can be understood as cognitive declines that are associated with healthy aging (referring to as age-related cognitive decline).

To exemplify the principal cognitive disorders, the inventors use here the criteria of the DSM-5™ that refer to neurodevelopmental disorders and neurocognitive disorders However, this is not an exclusive description of cognitive disorders but encompass similar disorders described in other diagnostic manuals including but not limited to the ICD-10 Classification of Mental and Behavioral Disorders and more generally all the disorders primarily associated with an impairment of cognitive abilities.

In this respect, cognitive disorders encompass neurodevelopmental disorders and neurocognitive disorders.

Neurodevelopmental disorders refer to disorders that manifest early in development, often before the child enters grade school. They are characterized by developmental abnormalities that produce impairments of conceptual, practical and social functioning. Consequently, the individual fails to meet age-matched standards of intellectual development, academic achievement, personal independence and/or social participation. The range of developmental deficits varies from very specific limitations of learning or of executive functions to global impairments of social skills or intelligence.

Neurodevelopmental disorders can be associated with a specific cause (e.g. a known genetic condition or environmental factor) or can be unspecified when the etiology is not known. Examples of specifiers include genetic disorders such as, but not limited to, Down syndrome, fragile X syndrome, tuberous sclerosis, Rett syndrome, William syndrome, spina bifida. Medical conditions include pathologies such as epilepsy, metabolic diseases; developmental anomalies (e.g. brain malformations), maternal diseases (e.g. placental disease) or perinatal environmental factors (e.g. fetal exposure to alcohol, toxins or teratogens).

Neurodevelopmental disorders include seven categories of disorders that are specified as follows:

1. Intellectual disabilities are characterized by deficits in general mental abilities, such as reasoning, problem solving, planning, abstract thinking, judgment, academic learning, and learning from experience. Global Developmental Delay is diagnosed for individuals who are unable to undergo systematic assessments of intellectual functioning, including children who are too young to participate in standardized testing.
2. Communication disorders include deficits in language (i.e. use of a conventional system of symbols for communication), speech (i.e. expression of thoughts by articulated sounds) as well as verbal and non-verbal communication. This category includes language disorder, speech sound disorder, childhood-onset fluency disorder (Stuttering), social (pragmatic) communication disorder and unspecified communication disorder.
3. Autism spectrum disorder is characterized by persistent deficits in social communication and interaction, restricted interests and repetitive behaviors. Autism spectrum disorder also refers to as autistic disorder, Asperger's disorder, or pervasive developmental disorder.
4. Attention-Deficit/Hyperactivity Disorder (ADHD) is associated with marked inattention and/or hyperactivity and impulsivity that is inconsistent with the expected developmental level and that directly impacts on social and academic/occupational activities. The symptoms are not solely a manifestation of oppositional behavior, defiance, hostility, or failure to understand tasks or instructions.
5. Specific learning disorder is characterized by specific deficits in ability to perceive or process information efficiently and accurately. It relates to persistent difficulties in learning and using academic skills in on or more domains among reading (e.g. dyslexia), written expression (e.g. dysgraphia) and mathematics (e.g. dyscalculia).
6. Neurodevelopmental motor disorders are characterized by abnormal involuntary or uncontrollable movements of the body. These disorders can cause lack of intended movements or excess of involuntary movements. More specifically, motor disorders can be developmental coordination disorder (deficits in the acquisition and execution of coordinated motor skills), stereotypic movement disorder (repetitive, seemingly driven, and apparently purposeless motor behaviors) and tic disorders (stereotyped motor movements or vocalizations which are sudden, rapid, recurrent and nonrhythmic). The duration, presumed etiology and clinical presentation define the specific tic disorder that is diagnosed (e.g Tourette's disorder).
7. Other neurodevelopmental disorders apply when symptoms are characteristic of a neurodevelopmental disorder but do not meet the full criteria for any of the disorders in the neurodevelopmental disorders diagnostic class.

Of note, the neurodevelopmental disorders frequently co-occur; for example, individuals with autism spectrum disorder often have intellectual disability, and many children with ADHD also have a specific learning disorder.

Neurodevelopmental disorders should be diagnosed by a clinician on the basis of DSM-5™ diagnostic criteria or of any other mental health diagnostic tool. The tests used to evaluate the nature and degree of impairments could be selected among the ones evaluating intellectual functioning and/or adaptive behaviors. The relevant tests should be selected according to the age of the patient and the nature and severity of the suspected impairments. Non-exhaustive examples of scales assessing global or specific functions and that are validated including for pediatric populations are specified below.

- Scales assessing the global cognitive health (Hessl et al., 2016; Esbensen et al., 2017):
  - The CANTAB batteries of tests
  - The NIH Toolbox Cognitive Battery for Intellectual Disabilities
- Scales assessing independent functioning and adaptive behaviors (Berry-Kravis et al., 2013; Esbensen et al., 2017):
  - Adaptive Behavior Assessment System—Third Edition (ABAS-III) or latest
  - Aberrant Behavior Checklist (ABC)
  - Vineland Adaptive Behavior Scales (VABS)
  - Connors Rating Scales
- Scales assessing patient's quality of life (Varni et al., 2001; Burckhardt and Anderson, 2003):
  - Pediatric Quality of Life Inventory (PedsQL)
  - The Quality of Life Scale (QOLS)
- Scales assessing specific functions
  - Executive functions: Behavior Rating Inventory of Executive Functions inventories (BRIEF), Wisconsin Card Sorting Test (WCST), Virtual radial maze (working memory procedure) (Marighetto et al., 2012)
  - Learning and memory: Virtual radial maze (declarative/relational memory procedure) (Sellami et al., 2017)
  - Social cognition: Social Responsiveness Scale
  - Language: Boston Naming Test (BNT), Token Test
  - Quality of sleep: Pittsburgh Sleep Quality Index (PSQI)

Neurocognitive disorders refer to mental disorders characterized by primary clinical deficits in the cognitive function. These deficits should be acquired rather than developmental, representing a decline from a previously attained cognitive level. The cognitive deficits associated with neurocognitive disorders should impact on individual's everyday life activities and can lead to loss of autonomy. Neurocognitive disorders may affect one or more cognitive domains among complex attention, executive functions, learning and memory, language, perceptual motor/visuospatial functions and social cognition.

Neurocognitive disorders can be caused by different pathologies including, but not limited to, neurodegenerative diseases (e.g. Alzheimer disease, frontotemporal lobar degeneration, Lewy body degeneration Parkinson disease, or Huntington disease), vascular disease, traumatic brain injury, substance/medication use, human immunodeficiency virus (HIV) infection, prion disease.

Neurocognitive disorders are categorized as follows:

1. Delirium: refers to disturbances in cognition that develops over a short period of time (hours). Delirium is a direct consequence of another medical condition or of substance intoxication or withdrawal (e.g. a drug of abuse, a medication, a toxin). Delirium can last few hours to several months.
2. Major and mild neurocognitive disorders: refer to a cognitive decline (in one or more cognitive domains) that interferes with independence in everyday life activities. Major neurocognitive disorders (also referring to as dementia) are characterized by a significant loss of autonomy. Typically, individuals require assistance at minimum to performs complex tasks such as managing medication or paying bills. Mild neurocognitive disorders (also referring to as mild cognitive impairment) are characterized by weaker cognitive decline than major neurocognitive disorders. Mild neurocognitive disorders do not prevent individual's autonomy but achieving complex tasks of daily living requires greater effort or compensation strategies.

Moreover, unspecified mild or major neurocognitive disorder can be diagnosed when the patient manifests symptoms of cognitive deficits that cannot be associated with a precise etiology.

Diagnosis of neurocognitive disorders should be performed by the clinician using subjective and/or objective assessments of the cognitive function. Subjective cognitive assessment consists in obtaining information from the patient and/or caregivers on changes in cognitive functioning as manifested in everyday activities (e.g. managing finances and medication).

Objective assessment should be conducted using one or more standardized tests aiming at assessing cognitive functions. Several scales are available (Sheehan, 2012). Some are dedicated to the inventory of activities of daily living such as the Functional Activities Questionnaire or quality of life such as the Quality of Life Scale (QOLS). Others assess specific cognitive functions or the global cognitive functioning Non-exhaustive examples of global cognitive tests are the Mini-Mental State Examination, the Short Test of Mental Status, the Montreal Cognitive Assessment, the Mini-Cog tests, the CANTAB series of tests, Repeatable Battery for Assessment of Neuropsychological Status (RBANS) and the NIH Toolbox Cognition Batteries.

Furthermore, the virtual radial maze procedures developed by A. Marighetto and colleagues are able to detect subtle working memory and declarative/relational memory deficits associated with normal and pathological ageing (Etchamendy et al., 2012; Marighetto et al., 2012; Sellami et al., 2017). These radial maze procedures have matching equivalents in rodents, allowing to improve translation of therapeutic candidates for the treatment of cognitive disorders from animals to human patients.

Hence, the present invention relates to a compound of Formula (I):

Formula (I)

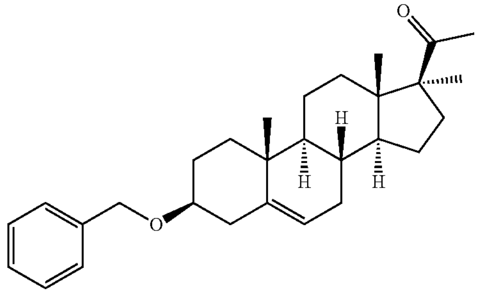

for use in the prevention or treatment of a cognitive disorder selected among neurodevelopmental disorders, neurocognitive disorders and age-related cognitive decline. Administration to a subject of an effective amount of compound of Formula (I) reduces, abrogates, stabilizes (i.e. prevents or limit the worsening of) the cognitive disorder or impairment. Thus, a subject treated with an effective treatment regimen displays an improvement following subjective clinical examination or in one or several parameters of the neuropsychological tests or of the quality of life scales relevant to subject's pathology, age, language and culture. Alternatively, treatment of a subject with an effective regimen of compound of Formula (I) preserves cognitive function so that it prevents or slows down the decline upon first presentation or diagnosis, as compared to the expected decline in the absence of treatment.

The terms "3β-benzyloxy, 17α-methyl-pregn-5-en-20-one" or "$C_{29}H_{40}O_2$" or "3Bn17MeP" or "1-((3S,8R,9S,10R,13S,14S,17S)-3-(benzyloxy)-10,13,17-trimethyl-2,3,4,7,8,9,10,11,12,13,14,15,16,17-tetradecahydro-1H-cyclopenta[a]phenanthren-17-yl)ethan-1-one" designate the pregnenolone derivative according to the present invention which has the following formula (I):

Formula (I)

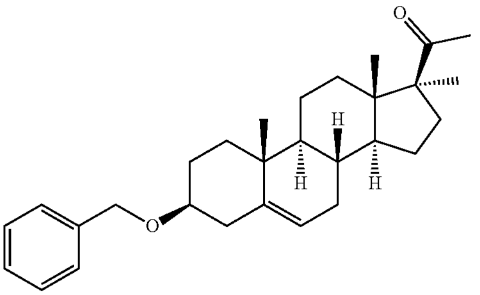

Process for the Manufacture

The present invention also relates to process for the manufacture of the compound of the invention. The compound of Formula (I) can be obtained by different synthetic pathways as we can see below.

First, compound 3β-benzyloxy-17α-methyl-pregn-5-en-20-one can be obtained in 2 chemical steps from pregnenolone (Route A).

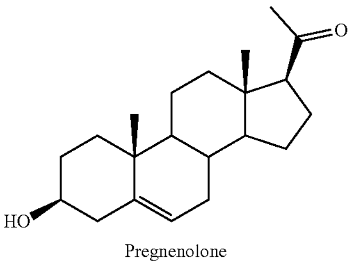 [SMILES: CC(=O)[C@H]1CCC2C3CC=C4C[C@@H](O)CC[C@]4(C)C3CC[C@@]21C]

Pregnenolone

Introduction of the Methyl group at the C17 position is carried out by reaction between an enol acetate intermediate, allowed by reaction of pregnenolone and acetic anhydride, and a Grignard reagent to obtain compound of formula (II)

Formula (II)

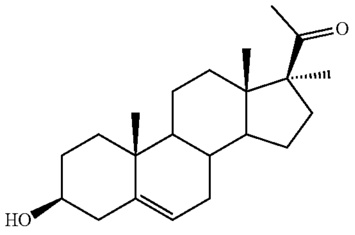

Then, hydroxyl group at C3 is benzylated with 2-benzyloxy-1-methylpyridinium triflate reagent to afford 3β-benzyloxy-17α-methyl-pregn-5-en-20-one of formula (I).

Formula (I)

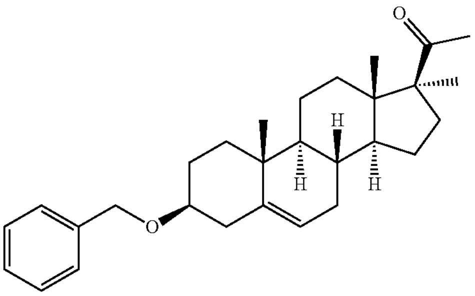

As we can see on FIGS. 1-4 and as described below other pathways can be used to afford 3β-benzyloxy-17α-methyl-pregn-5-en-20-one.

For example, the last stage alkylation of the hydroxyl group at the C3 position can be done under basic conditions (NaH, t-BuOK or other bases) in the presence of benzyl chloride or benzyl bromide (route B). Alkylation under acidic media using trichloroacetimidate in the presence of catalytic amount of an organic acid can also be carried out.

Another way (route C) can start with the protection of pregnenolone ketone function via an acetal to give compound of formula (III).

Formula (III)

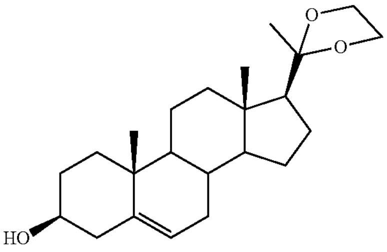

The free alcohol is then be alkylated by a benzyl group (under acidic or basic condition or via 2-benzyloxy-1-methylpyridinium triflate as described above) to give compound of Formula (IV).

Formula (IV)

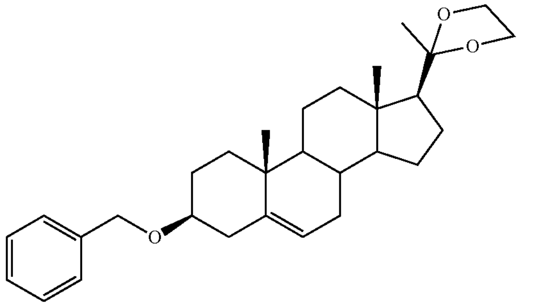

The acetal is hydrolysed under acidic conditions to give compound of formula (V).

Formula (V)

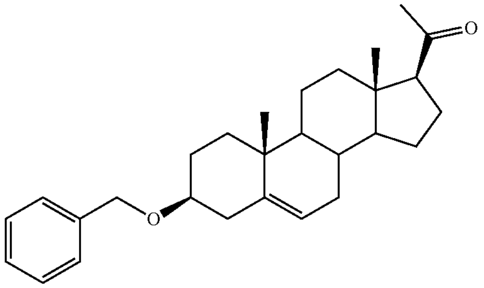

Direct methylation using methyl iodide in the presence of sodium hydride gives 3β-benzyloxy, 17α-methyl-pregn-5-en-20-one of formula (I).

Formula (I)

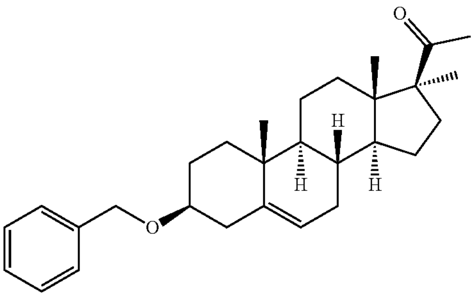

Another alternative is to perform route C without protection of the pregnenolone ketone group (Route D).

The present invention also concerns a pharmaceutical composition comprising a compound of Formula (I):

Formula (I)

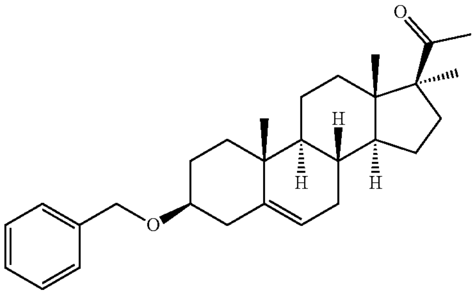

and at least one pharmaceutically acceptable excipient.

The form of the pharmaceutical composition, the route of administration, the dosage and the regimen naturally depend upon the condition to be treated, the severity of the illness, the age, weight, and sex of the patient, etc.

While it is possible for the compound of the present invention to be administered alone, it is preferable to formulate it into a pharmaceutical composition in accordance with standard pharmaceutical practice. Thus, the invention also provides a pharmaceutical composition comprising a compound of formula (I) in admixture with at least one pharmaceutically acceptable excipient.

There is further provided by the present invention a process of preparing a pharmaceutical composition, which process comprises mixing a compound of Formula (I), together with at least one pharmaceutically acceptable excipient.

The pharmaceutical composition will typically comprise at least one pharmaceutically acceptable excipient. Acceptable excipients for therapeutic use are well known in the pharmaceutical art, and are described, for example, in Remington's Pharmaceutical Sciences, 21st Edition 2011. The choice of pharmaceutical excipient can be selected with regard to the intended route of administration and standard pharmaceutical practice. The excipient must be acceptable in the sense of being not deleterious to the recipient thereof. The at least one pharmaceutically acceptable excipient may be for example, a binder, a diluent, a carrier, a lubricant, a disintegrator, a wetting agent, a dispersing agent, a suspending agent, and the like.

The routes for administration (delivery) of the above defined compound include, but are not limited to: oral (eg as a tablet, capsule, or as an ingestible solution), topical, mucosal (e. g. as a nasal spray or aerosol for inhalation), nasal, gastrointestinal, intraspinal, intraperitoneal, intramuscular, intravenous, intrauterine, intraocular, intradermal, intracranial, intratracheal, intravaginal, intracere broventricular, intracerebral, subcutaneous, ophthalmic (including intravitreal or intracameral), transdermal, rectal, buccal, epidural, sublingual.

Preferred administration routes include oral, mucosal, parenteral, and sublingual.

For example, the compound can be administered orally in the form of tablets, coated tablets, pills, capsules, soft gelatin capsules, oral powders, granules, ovules, elixirs, solutions or suspensions, which may contain flavouring or colouring agents, for immediate-, delayed-, modified-, sustained-, pulsed- or controlled-release applications.

The tablets may contain excipients such as microcrystalline cellulose, lactose, sodium citrate, calcium carbonate, dibasic calcium phosphate and glycine, a disintegrant such as starch (preferably corn, potato or tapioca starch), sodium starch glycollate, croscarmellose sodium and certain complex silicates, a binder such as polyvinylpyrrolidone, hydroxypropylmethylcellulose (HPMC), hydroxypropylcellulose (HPC), sucrose, gelatin and acacia, a lubricant such as magnesium stearate, stearic acid, glyceryl behenate. Solid compositions of a similar type may also be employed as fillers in hard gelatin capsules. Preferred excipients in this regard include lactose, saccharose, sorbitol, mannitol, potato starch, corn starch, amylopectin, cellulose derivatives or gelatin. Hard gelatin capsules may contain granules of the compound of the invention.

Soft gelatin capsules may be prepared with capsules containing the compound of the invention, vegetable oil, waxes, fat, or other suitable vehicle for soft gelatin capsules. As an example, the acceptable vehicle can be an oleaginous vehicle, such as a long chain triglyceride vegetable oil (e.g. corn oil).

Dispersible powders and granules suitable for preparation of an aqueous suspension by the addition of water may contain the active ingredient in a mixture with dispersing agents, wetting agents, and suspending agents and one or more preservatives additional excipients, for example sweetening, flavoring and coloring agents, may also be present. These compositions may be preserved by the addition of an anti-oxidant such as ascorbic acid.

Liquid dosage forms for oral administration may include pharmaceutically acceptable, solutions, emulsions, suspensions, syrups, and elixirs containing inert diluents commonly used in the art, such as water or an oleaginous vehicle. Liquid dosage form may be presented as a dry product for constitution with water or other suitable vehicle before use. Such compositions may also comprise adjuvants, such as wetting agents, emulsifying and suspending agents, complexing agents such as 2-hydroxypropyl-beta-cyclodextrin, sulfobutylether-beta-cylodextrin, and sweetening, flavouring, perfuming agents, colouring matter or dyes with diluents such as water, ethanol, propylene glycol and glycerin, and combinations thereof. These compositions may be preserved by the addition of an anti-oxidant such as butylated hydroxyanisol or alpha-tocopherol.

Finely divided powder of the compounds of the invention may be prepared by for example by micronisation or by processes known in the art. The compounds of the invention may be milled using known milling procedures such as wet milling to obtain a particle size appropriate for tablet formation and for other formulation types.

If the compound of the present invention is administered parenterally, then examples of such administration include one or more of: intravenously, intraarterially, intraperitoneally, intrathecally, intraventricularly, intraurethrally, intrasternally, intracranially, intramuscularly or subcutaneously administering the agent; and/or by using infusion techniques.

The compound of the invention can be administered via the parenteral route with a readily available or a depot-type formulation.

The pharmaceutical compositions for the parenteral administration of a readily available formulation may be in the form of a sterile injectable aqueous or oleagenous solution or suspension in a non-toxic parenterally-acceptable diluent or solvent and may contain formulatory agents such as suspending, stabilising dispersing, wetting and/or complexing agents such as cyclodextrin e.g. 2-hydroxypropyl-beta-cyclodextrin, sulfobutylether-beta-cylodextrin.

The depot-type formulation for the parenteral administration may be prepared by conventional techniques with pharmaceutically acceptable excipient including without being limited to, biocompatible and biodegradable polymers (e.g. poly(β-caprolactone), poly(ethylene oxide), poly(glycolic acid), poly[(lactic acid)-co-(glycolic acid) . . . )], poly(lactic acid) . . . ), non-biodegradable polymers (e.g. ethylene vinylacetate copolymer, polyurethane, polyester (amide), polyvinyl chloride . . . ) aqueous and non-aqueous vehicles (e.g water, sesame oil, cottonseed oil, soybean oil, castor oil, almond oil, oily esters, ethyl alcohol or fractionated vegetable oils, propylene glycol, DMSO, THF, 2-pyrrolidone, N-methylpyrrolidinone, N-vinylpyrrolidinone . . . ).

Alternatively, the active ingredient may be in dry form such as a powder, crystalline or freeze-dried solid for constitution with a suitable vehicle. The preparation of suitable parenteral formulations under sterile conditions is readily accomplished by standard pharmaceutical techniques well known to those skilled in the art.

As indicated, the compound of the present invention can be administered intranasally or by inhalation and is conveniently delivered in the form of a dry powder inhaler or an aerosol spray presentation from a pressurised container, pump, spray or nebuliser with the use of a suitable propellant, e.g. dichlorodifluoromethane, trichlorofluoromethane, dichlorotetrafluoroethane, (for example from Ineos Fluor), carbon dioxide or other suitable gas. In the case of a pressurised aerosol, the dosage unit may be determined by providing a valve to deliver a metered amount. The pressurised container, pump, spray or nebuliser may contain a solution or suspension of the active compound. Capsules and cartridges (made, for example, from gelatin) for use in an inhaler or insufflator may be formulated to contain a powder mix of the compound and a suitable powder base such as lactose or starch. For compositions suitable and/or adapted for inhaled administration, it is preferred that the compound or salt of formula (I) is in a particle-size-reduced form, and more preferably the size-reduced form is obtained or obtainable by micronisation. The preferable particle size of the size-reduced (e.g. micronised) compound or salt or solvate is defined by a D50 value of about 0.5 to about 50 microns (for example as measured using laser diffraction).

Alternatively, the compound of the present invention can be administered in the form of a suppository or pessary, or it may be applied topically in the form of a gel, hydrogel, lotion, solution, cream, ointment or dusting powder. The compound of the present invention may also be dermally or transdermally administered, for example, by the use of a skin patch. They may also be administered by the pulmonary or rectal routes. They may also be administered by the ocular route. For ophthalmic use, the compounds can be formulated as micronised suspensions in isotonic, pH adjusted, sterile saline, or, preferably, as solutions in isotonic, pH adjusted, sterile saline, optionally in combination with a preservative such as a benzylalkonium chloride. Alternatively, they may be formulated in an ointment such as petrolatum.

For application topically to the skin, the agent of the present invention can be formulated as a suitable ointment containing the active compound suspended or dissolved in, for example, a mixture with one or more of the following: mineral oil, liquid petrolatum, white petrolatum, propylene glycol, polyoxyethylene polyoxypropylene compound, emulsifying wax and water. Alternatively, it can be formulated as a suitable lotion or cream, suspended or dissolved in, for example, a mixture of one or more of the following: mineral oil, sorbitan monostearate, a polyethylene glycol, liquid paraffin, polysorbate 60, cetyl esters wax, cetearyl alcohol, 2-octyldodecanol, benzyl alcohol and water.

Typically, a physician will determine the actual dosage which will be most suitable for an individual subject. The specific dose level and frequency of dosage for any particular individual may be varied and will depend upon a variety of factors including the activity of the specific compound employed and length of action of that compound, the age, body weight, general health, sex, diet, mode and time of administration, rate of excretion, drug combination, the severity of the particular condition, and the individual undergoing therapy.

The above defined compound may be administered to a subject for its use in the treatment of cognitive disorders at any dose suitable for obtaining a therapeutic effect For oral and parenteral administration to humans, the daily dosage level of the agent may be in single or divided doses.

A proposed range of dose of the compound according to the present invention for administration to a human (of approximately 70 kg body weight) is, including but not limited, 1 μg to 1000 mg, more typically 1 μg to 500 mg, more typically 1 μg to 100 mg, more typically 1 μg to 50 mg, more typically 1 μg to 10 mg, more typically 1 μg to 5 mg, more typically 1 μg to 1 mg, more typically 1 μg to 600 μg, more typically 1 μg to 200 μg, more typically 1 μg to 100 μg, more typically 1 μg to 60 μg, more typically 10 μg to 1000 mg, more typically 10 μg to 500 mg , more typically 10 μg to 100 mg, more typically 10 μg to 50 mg, more typically 10 μg to 10 mg, more typically 10 μg to 5 mg, more typically 10 μg to 1 mg, more typically 10 μg to 600 μg, more typically 10 μg to 200 μg, more typically 10 μg to 100 μg, more typically 20 μg to 1000 mg, more typically 20 μg to 600 mg , more typically 20 μg to 200 mg, more typically 20 μg to 60 mg, more typically 20 μg to 20 mg, more typically 20 μg to 6 mg, more typically 20 μg to 2 mg, more typically 20 μg to 600 μg, more typically 20 μg to 200 μg of the active ingredient per unit dose, expressed as the weight of free acid. The unit dose may be administered, for example, 1 to 4 times per day. The dose will depend on the route of administration. It will be appreciated that it may be necessary to make routine variations to the dosage depending on the age and weight of the patient as well as the severity of the condition. The dosage will also depend on the route of administration. The precise dose and route of administration will ultimately be at the discretion of the attendant physician or veterinarian.

A "suitable dose", an "effective amount" of the compound of the invention refers to the effective amount sufficient to prevent, reduce, eliminate, control, treat or inhibit a cognitive disorder. The term "controlling" is intended to refer to all processes wherein there may be a slowing, interrupting, arresting, or stopping the progression of the diseases and conditions described herein but does not necessarily indicate a total elimination of all disease and condition symptoms. The doses used for the administration can be adapted as a function of various parameters, in particular as a function of the mode of administration used, of the relevant pathology, or alternatively of the desired duration of treatment. Naturally, the form of the pharmaceutical composition, the route of administration, the dosage and the regimen naturally depend on the condition to be treated, the severity of the illness, the age, weight, and sex of the subject, etc. The ranges of effective doses provided below are not intended to limit the invention and represent preferred dose ranges. However, the preferred dose can be tailored to the individual subject, as is understood and determinable by one of skill in the art, without undue experimentation.

The invention also concerns a method of treating cognitive disorders in a subject in need thereof comprising the administration of an effective amount of the compound of Formula (I):

Formula (I)

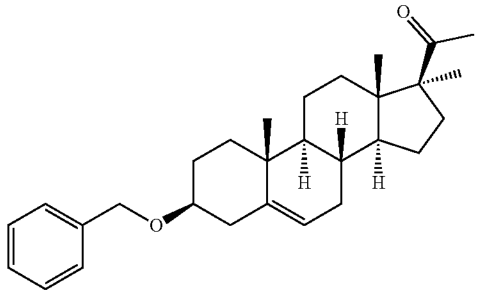

to said patient.

All the embodiment disclosed above are encompassed in this aspect.

In another aspect, the present invention relates to the use of the compound of Formula (I):

Formula (I)

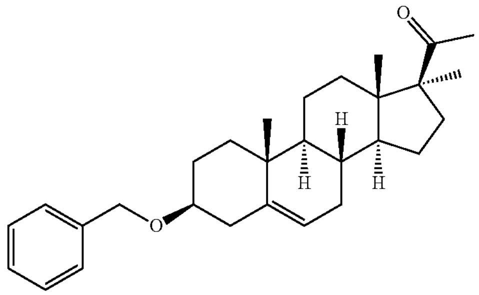

for the treatment of cognitive disorders.

All the embodiment disclosed above are encompassed in this aspect.

In a further embodiment, the present invention relates to the use of the compound of Formula (I):

Formula (I)

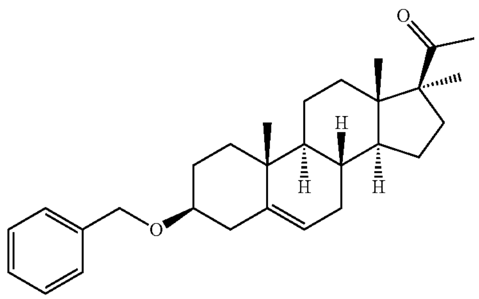

for the manufacture of a pharmaceutical preparation for the treatment of cognitive disorders.

All the embodiment disclosed above are encompassed in this aspect.

EXAMPLES

Example 1

Synthesis of 3Bn17MeP

3β-benzyloxy, 17α-methyl-pregn-5-en-20-one (3Bn17MeP) is a chemical entity containing 7 chiral centers 3S, 8S, 9S, 10R, 13S, 14S, 17S as described in Formula (I):

Formula (I)

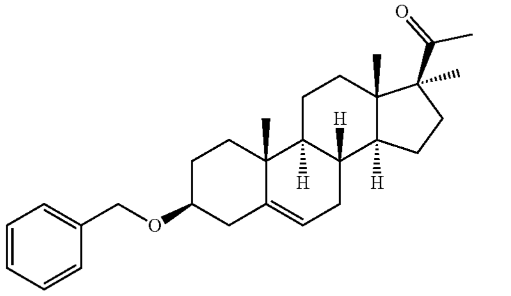

The stereochemical configuration at these centers is identical to those of the starting material pregnenolone.

This example is the mode of preparation of 3β-benzyloxy, 17α-methyl-pregn-5-en-20-one (3Bn17MeP) following route A of FIG. 1.

Synthesis of the Enol Acetate Intermediate

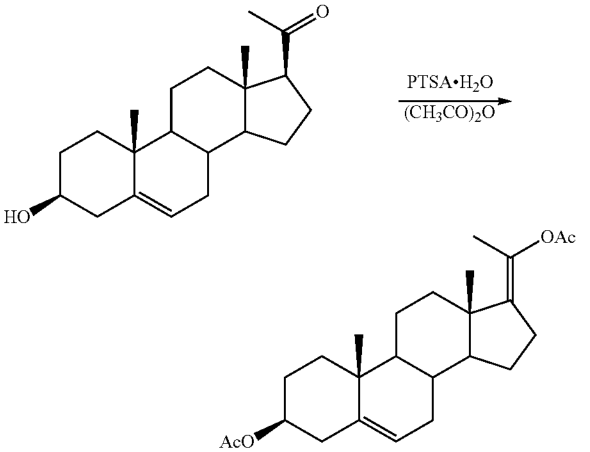

p-Toluenesulfonic acid monohydrate (1.12 g; 5.9 mmol; 0.93 eq.) was added to a solution of Pregnenolone (2 g; 6.3 mmol; 1 eq.) in acetic anhydride (230 ml). The reaction medium was stirred for 5 h at reflux and acetic anhydride was slowly distilled off. After allowing to cool to 20° C., the reaction medium was poured into crushed ice then the mixture was extracted with diethyl ether. The organic layer was washed with saturated aqueous $Na_2CO_3$, dried over $Na_2SO_4$ then evaporated under reduced pressure. The residue was purified by chromatography on silica gel (eluent: cyclohexane/AcOEt from 100/0 to 90/10) to give the Pregnenolone enol acetate (2.2 g; 85%) as a white solid.

Synthesis of the 17α-methyl-pregnenolone

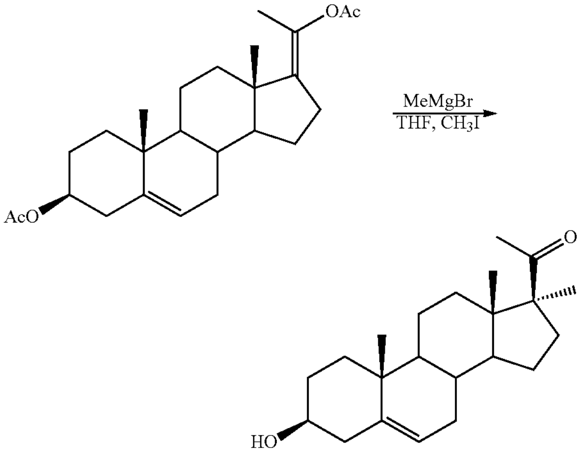

As shown below, $MeMgBr_2$ (3M in $Et_2O$; 25 ml; 75 mmol; 10 eq.) was added to a solution of pregnenolone enol acetate (3 g; 7.5 mmol; 1 eq.) in anhydrous Tetrahydrofuran (65 ml). The reaction medium was stirred for 1 h at reflux, then allowed to cool to 20° C. $CH_3I$ (4.6 ml; 75 mmol; 10 eq.) was added and reaction medium was stirred at reflux. Adding $CH_3I$ was repeated every 45 minutes until 40 equivalents. After cooling to 20° C., an aqueous solution of $NH_4Cl$ was added and the mixture was extracted with ethyl acetate. The organic layer was washed with brine, dried over $Na_2SO_4$ then evaporated under reduced pressure. The residue was purified by chromatography on silica gel (eluent: cyclohexane/AcOEt 75/25) to give the 17α-methyl-pregnenolone (~600 mg; 25%) as a white solid.

Synthesis of the 3β-(benzyloxy)-17α-methyl-pregn-5-en-20-one

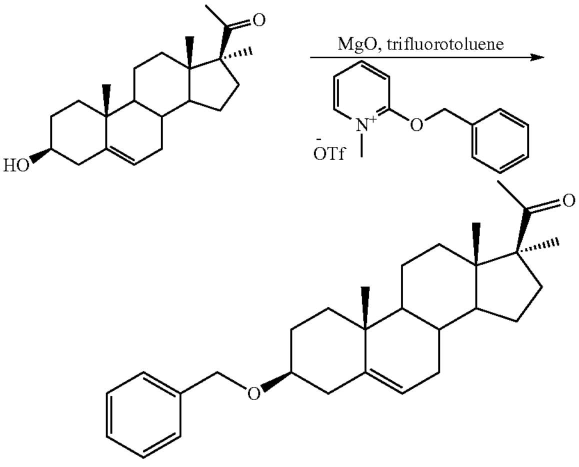

MgO (100 mg; 2.42 mmol; 2 eq.) and 2-benzyloxy-1-methylpridinium triflate (850 mg; 2.42 mmol; 2.0 eq.) were added to a solution of 17α-methyl-pregnenolone (400 mg; 1.21 mmol; 1 eq.) in trifluorotoluene (10 ml). The reaction medium was stirred for one night at 85° C., then filtered on celite and evaporated under reduced pressure. The residue was purified by chromatography on silica gel (eluent: cyclohexane/AcOEt 95/5) then by crystallisation in acetone to give the 3β-(benzyloxy)-17α-methyl-pregn-5-en-20-one (0.28 g; 36%) as a white solid.

Example 2

Specific Inhibition of the Activity of the CB1 Receptor by 3Bn17MeP

The understanding of the effects of the compound of the present invention, 3Bn17MeP, on cellular activities has been conducted by studying its capacity to inhibit several effects induced by CB1 stimulation. In particular, the capacity of 3Bn17MeP (i) to suppress the inhibition of cellular respiration, (ii) to inhibit the increase in phosphorylation of Erk1/$2^{MAPK}$ (p-Erk1/$2^{MAPK}$, extracellular signal-regulated kinases from the mitogen-activated protein kinases family) and (iii) to prevent the inhibition of cyclic adenosine monophosphate (cAMP) induced CB1 receptor stimulation with $\Delta^9$-tetrahydrocannabinol (THC) have been studied. Cellular respiration, p-Erk1/$2^{MAPK}$ and cAMP have been studied because these cellular responses determine the signaling-specific inhibition of CB1 receptor activity by pregnenolone (Vallée et al., 2014). That is, pregnenolone blocks THC-induced inhibition of cellular respiration, inhibits THC-induced increase in p-Erk1/$2^{MAPK}$ but has no effect on THC-induced inhibition of cAMP. Conversely, orthosteric CB1 antagonists such as rimonabant inhibit both responses. The selectivity of the effects of 3Bn17MeP on the CB1 receptor was studied by analysing the binding this compound on 85 receptors.

Materials and Methods

Effect of 3Bn17MeP on the Inhibition of Cellular Respiration Induced by THC:

The aim of these studies was to assess the effect of 3Bn17MeP on the inhibition of cellular respiration induced by THC (1 μM) in HEK-293 cells transiently transfected with the human CB1 receptors (hCB1). HEK-293 cells were chosen because they do not express endogenous CB1 receptors, they can be easily transfected and have been previously used in experiments studying the in vitro activity of the CB1 receptor (Shore et al., 2014) and in experiments showing that pregnenolone is able to inhibit THC-induced decrease in cellular respiration (Vallée et al., 2014).

In a first study (FIG. 5A), HEK-293 cells were transiently transfected with the wild-type hCB1-expressing plasmid (HEK-293-hCB1-WT). Cells were first treated with 3Bn17MeP (0; 1; 2.5; 5; 50 and 100 nM dissolved in acetonitrile 0.01%). After 15 min of incubation, THC (0; 1 μM, dissolved in EtOH, 0.0034%) was added in the culture dishes for 30 minutes.

In a second study (FIG. 5B), HEK-293 cells were transiently transfected either with the wild-type hCB1-expressing plasmid (HEK-293-hCB1-WT) or with the mutant hCB1p.E1.49G-expressing plasmid (HEK-293-hCB1-Mut). In this mutant the glutamate amino acid at position 1.49 was substituted by a glycine. This mutation was shown to preserve the effect of THC but to suppress the effect of pregnenolone on cellular activities induced by CB1 receptor stimulation (Vallée et al., 2014). Indeed, the glutamate in position 1.49 is essential for the binding of pregnenolone to the CB1 receptor. Cells were first treated with 3Bn17MeP (100 nM dissolved in acetonitrile 0.01%). After 15 min of incubation, THC (0; 1 μM, dissolved in EtOH, 0.0034%) was added in the culture dishes for 30 minutes.

Cellular respiration was measured in a calibrated oxygraph equipped with a Clark electrode. Oxygen consumption (OC) rate was used to measure cellular respiration. The effects of THC on OC rate, in absence and in presence of 3Bn17MeP, were expressed as percentages of the baseline OC of the cell treated with the vehicle of 3Bn17MeP and the vehicle of THC from the same experiment.

Effect of 3Bn17MeP on the Increase in p-Erk1/$2^{MAPK}$ 0 Induced by THC

The aim of this study was to assess the effects of 3Bn17MeP on the increase in the phosphorylation of p-Erk1/$2^{MAPK}$ induced by the administration of THC in the STHdh$^{Q7/Q7}$ cell line (Striatal-derived cell line from a knock-in transgenic mouse containing homozygous Huntingtin loci with a humanized Exon 1 with 7 polyglutamine repeats). STHdh$^{Q7/Q7}$ cells were chosen because they stably express high levels of endogenous CB1 receptors. These cells have been previously used in experiments studying the in vitro activity of CB1 receptors following stimulation by endocannabinoids (Laprairie et al., 2014) and in our conditions are the ones allowing the most reliable analysis of CB1-induced increase in MAPK phosphorylation.

The effect of 3Bn17MeP at 5 doses (0.1; 0.3; 1; 3 and 9 μM; dissolved in DMSO 0.9%) was tested on the effects of THC at 10 μM (dissolved in DMSO 0.05%) on the phosphorylation of MAPK. Cells were pretreated with 3Bn17MeP or vehicle 30 minutes before being treated either with THC or vehicle for 30 min).

MAPK phosphorylation (p-Erk1/$2^{MAPK}$ proteins) was measured by AlphaLISA SureFire Ultra kits using the unphosphorylated Erk1/$2^{MAPK}$ proteins as loading controls. p-Erk1/$2^{MAPK}$ counts were normalized by calculating the percentage of increase of p-Erk1/$2^{MAPK}$ counts induced by THC or vehicle in absence and in presence of 3Bn17MeP.

Effect of 3Bn17MeP on the Inhibition of cAMP Induced by THC

The aim of this study was to assess the effects of 3Bn17MeP on the decrease in cAMP induced by THC administration in Chinese Hamster Ovary (CHO) cells stably expressing the human CB1 receptor CHO-hCB1.

CHO-hCB1 cells were chosen in these experiments because they do not endogenously express the CB1 receptor and have been previously used in experiments studying the effects of CB1 agonists (Rinaldi-Carmona et al., 1996), including THC, on cAMP and P-MAPK and in experiments showing that pregnenolone is able to inhibit THC-induced effects on P-MAPK but not on cAMP (Vallée et al., 2014).

Figure 5:
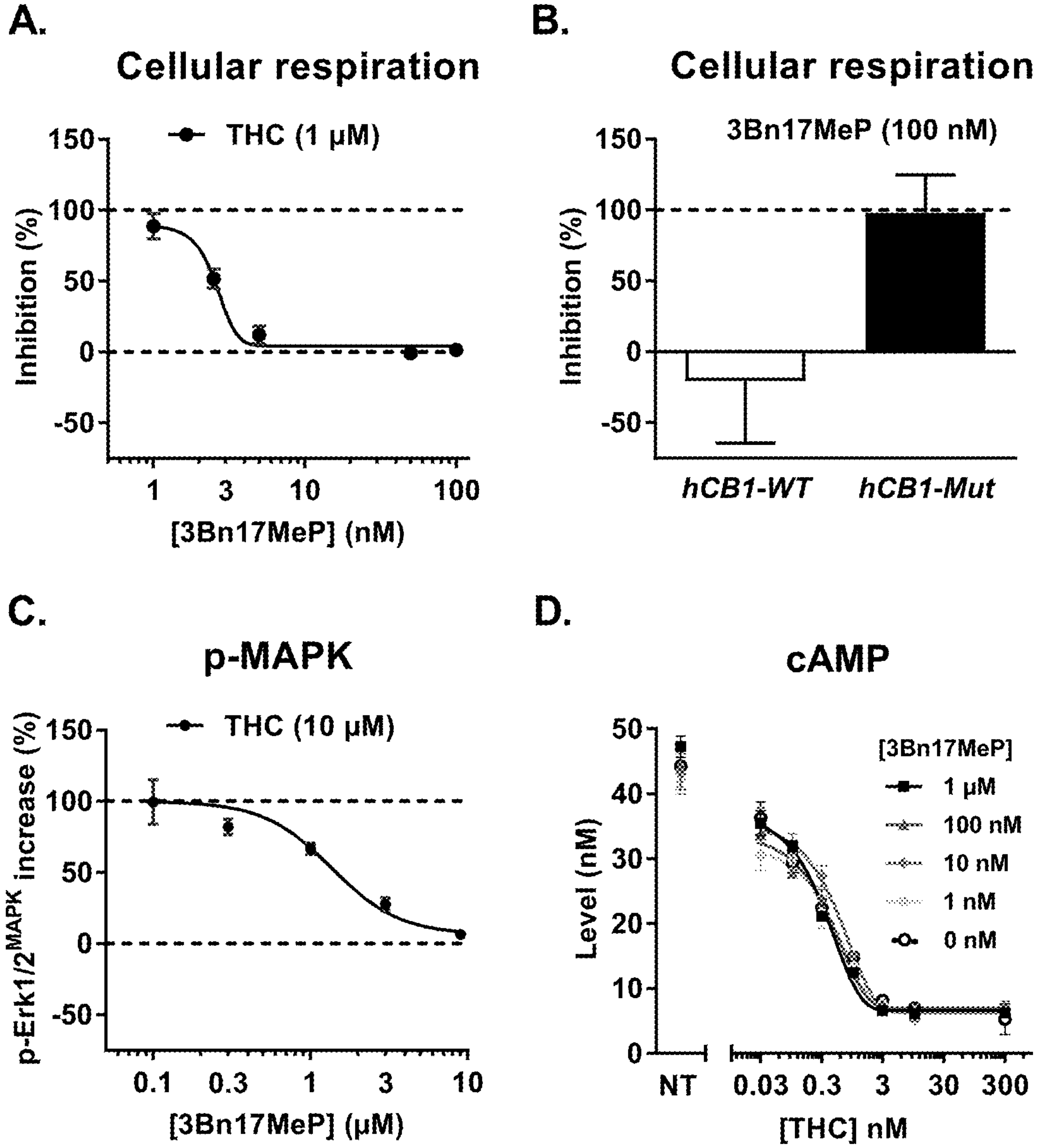
FIG. 5: In vitro effects of 3Bn17MeP on the inhibition of cellular respiration, on the increase in phosphorylation of mitogen-activated kinases (p-MAPK) and on the decrease of cyclic adenosine monophosphate (cAMP) induced by stimulation of CB1 receptors with $\Delta^9$-tetrahydrocannabinol (THC).

The effect of 3Bn17MeP (1 nM, 10 nM, 100 nM and 1 μM, dissolved in DMF (N,N-Dimethylformamide), 0.01%, FIG. 5C) was tested against a dose response function of THC (0.3, 1, 3, 10, 30, 100 and 300 nM, dissolved in ethanol, 0.0063%).

CHO-CB1-C2 cells were treated by concomitantly adding THC and the test compound for 45 minutes. Forskolin (2.5 μM) was also simultaneously added in all the conditions tested to sustain cAMP basal level.

At the end of the treatment, cells were lysed to proceed with the cAMP quantification. All measures were performed in triplicates in one experiment. The quantitative determination of cAMP was performed through a competitive fluorescence immunoassay. Data were expressed as % of Delta Fluorescence (Delta F) that was calculated as follows: Delta F %=(Sample Fluorescence−Negative control Fluorescence)/Negative control Fluorescence.

Binding Selectivity of 3Bn17MeP In Vitro:

The specificity of the effects of 3Bn17MeP on the CB1 receptor were studied by analysing the effects of this compound on the binding of other 85 receptors. This series of assays aimed to evaluate the binding specificity of 3Bn17MeP comparing it to the profile of pregnenolone.

The potential ability of 3Bn17MeP and pregnenolone, at a concentration of 10 μM, to displace the binding of ligands of 85 receptors (CEREP High-throughput profile+4 steroid receptors+Cannabinoid type 2 receptor) was tested. The CEREP High-throughput profile consists of a broad collection of 80 transmembrane and soluble receptors, ion channels and G-Protein coupled receptors. It has been specifically designed to provide information to prioritize the most promising compounds in hit-to-lead selection process. The androgen, estrogen, progesterone and PXR receptors and then Cannabinoid type 2 receptor were added to this assay in order to better tailor the assay to 3Bn17MeP completing the spectrum of steroid receptor already contained in the CEREP high-throughput profile.

Results

3Bn17MeP inhibits the decrease in cellular respiration induced by THC in HEK-293-hCB1-WT (FIG. 5A). At the $ID_{100}$ of 3Bn17MeP (50 nM), the effect of THC is fully abolished. In contrast, in HEK-293-hCB1-Mut THC-induced decrease in cellular respiration is insensitive to 3Bn17MeP (100 nM, FIG. 5B), indicating that 3Bn17MeP inhibits THC effect by interacting with CB1 receptors.

In $STHdh^{Q7/Q7}$ cells stably expressing endogenous CB1 receptors, 3Bn17MeP dose dependently decreases THC-induced MAPK phosphorylation (FIG. 5C), with an ED50 of approximately 1 μM.

In contrast, 3Bn17MeP does not modify the inhibition of cAMP induced by THC at any of the doses tested in CHO cells stably expressing the human CB1 receptors (FIG. 5D).

3Bn17MeP (10 μM) does not modify the binding of any of the 85 receptors that were tested in vitro using the CEREP High-throughput profile, including the major steroid receptors, the PXR receptors and the CB1 and the CB2 receptors (Table 1). In this respect 3Bn17MeP is more selective than pregnenolone (10 μM), which displaced (>80%) the binding of the glucocorticoid, androgen and progesterone receptors and to a lesser extent (>40%) the binding of the central and peripheral benzodiazepine receptors.

TABLE 1

Comparison between 3Bn17MeP and pregnenolone binding to 85 receptors

| | | % Inhibition | | | | % Inhibition | | | | % Inhibition | | | | % Inhibition | | | | Inhibition % | |
|---|---|---|---|---|---|---|---|---|---|---|---|---|---|---|---|---|---|---|---|
| FAMILY | ASSAY | PREG | 3Bn17 MeP | FAMILY | ASSAY | PREG | 3Bn17 MeP | FAMILY | ASSAY | PREG | 3Bn17 MeP | FAMILY | ASSAY | PREG | 3Bn17 MeP | FAMILY | ASSAY | PREG | 3Bn17 MeP |
| | | | | | | | | GPCRS | | | | | | | | Other receptors | | | |
| Adenosine | A1 | −25 | −27 | Dopamine | D1 | −8 | −10 | Neurokinin | NK1 | 17 | 8 | Serotonin | 5-HT1A | 12 | 25 | Benzodiazepine | BZD (periph) | 42 | 1 |
| | A2A | −1 | −6 | | D2S | 5 | 6 | | NK2 | −1 | −12 | | 5-HT1B | −28 | −15 | Cytokines | TNF-alpha | 4 | 4 |
| | A3 | 11 | 1 | | D3 | 11 | −2 | | NK3 | 11 | 7 | | 5-HT2A | −1 | −8 | GABA | GABA | 10 | 10 |
| Adrenergic | alpha1 | 1 | 5 | | D4.4 | 20 | −10 | Neuropetide Y | N1 | −11 | −32 | | 5-HT2B | −38 | 16 | | BZD [(central) | −43 | −16 |
| | alpha2 | −2 | −1 | | D5 | −4 | −6 | | Y2 | −9 | −6 | | 5-HT2C | −9 | 10 | | Cl- channel | 29 | 1 |
| | beta2 | −5 | −4 | Endothelin | ETA | −3 | 1 | Neuro-tensin | NTS1 (NT1) | −19 | −13 | | 5-HT5a | 11 | 2 | Glutamate | PCP | 5 | 5 |
| | beta1 | 4 | 7 | | ETB | 4 | −13 | Opioid and opioid-like | delta2 (DOP) | 9 | −3 | | 5-HT6 | 5 | −1 | Growth factors | PDGF | −15 | −13 |
| Angiotensin-II | AT1 | −28 | −13 | Galanin | GAL1 | −16 | −26 | | kappa (KOP) | 38 | −17 | | 5-HT7 | 11 | 8 | Purinergic channels | P2X | 13 | 8 |
| | AT2 | −18 | −5 | | GAL2 | 1 | −11 | | mu (MOP) | −5 | −4 | Ion channels | | | | Serotonin | 5-HT3 | 6 | 4 |
| Bombesin | BB | −18 | −6 | Histamine | H1 | 0 | 3 | | NOP (ORL1) | 2 | 2 | Ca2+ channels | Ca2+-L | −19 | 12 | Sigma | sigma | 26 | 9 |
| Bradykinin | B2 | −9 | 0 | | H2 | 9 | 12 | | EP2 | 24 | 19 | | KV | −23 | −15 | Nuclear receptors | | | |
| Calcitonin gene-related | CGRP | −12 | −15 | Melanocortin | MC4 | −15 | −10 | Prostanoid | EP4 | 21 | 25 | K+ channels | SKCa | −8 | −3 | Steroid nuclear receptors | GR | 88 | −2 |
| Cannabinoid | CB1 | 10 | 2 | Melatonin | MT1 (ML1A) | 26 | −8 | | IP (PGI2) | −12 | 0 | Na+ channels | Na+-site 2 | 23 | −12 | | AR | 95 | 16 |
| | CB2 | −19 | 2 | Muscarinic | M1 | −14 | −25 | Purinergic | P2Y | −3 | −2 | Transporters | | | | | ER | 26 | −5 |
| Chemokines | CXCR2 KIL-8B) | −10 | 0 | | M2 | −4 | −17 | Somato-statin | sst | −8 | −6 | Dopamine | dopamine | −12 | −23 | | PR | 87 | 20 |
| | CCR1 | −10 | −13 | | M3 | 2 | 16 | Vasoactive intestinal peptide | VPAC1 (VIP1) | −10 | −17 | Norepinephrine | norepinephrine | −12 | −1 | Non-steroid nuclear receptors | PPAR gamma | 4 | −12 |
| Cholecystokinin | CCK1 (CCKA) | −30 | 2 | | M4 | −4 | 2 | | PAC1-PACAP | −25 | −21, 2 | Serotonin | 5-HT trans. | 1 | 1 | | PXR | 15 | −8 |
| | CCK2 (CCKB) | −38 | −21 | | M5 | 8 | 0 | Vasopressin | V1a | 10 | 0 | | | | | | | | |

The in vitro effects of 3Bn17MeP are summarized in the table below:

TABLE 2

In vitro evaluation of the mechanism of action of 3Bn17MeP

| Effects of 3Bn17MeP on: | Test system | ID50 | ID100 | % inhibition |
|---|---|---|---|---|
| THC-induced decrease in cellular respiration | HEK-293-hCB1 | 2.5 nM | 50 nM | 100 |
| THC-induced increase in p-Erk1/$2^{MAPK}$ | $STHdh^{Q7/Q7}$ | 1 μM | 9 μM | ~100 |
| THC-induced decrease cAMP | CHO-hCB1 | — | — | — |
| CEREP High-throughput binding profile (85 receptors) | Receptor binding | >10 μM | — | NA |

NA = Not Analyzed because no effect was found

Conclusion

Hence, 3Bn17MeP in vitro acts as a Signaling-Specific inhibitor of the CB1 (CB1-SSi). Thus, 3Bn17MeP inhibits the decrease in cellular respiration induced by THC in HEK-293 transfected with the human CB1 receptors. 3Bn17MeP exerts its inhibitory effect on CB1 receptor stimulation through a binding a site which is different from the binding site of THC. 3Bn17MeP inhibits the increase in MAPK phosphorylation induced by THC in $STHdh^{Q7/Q7}$ cells endogenously expressing CB1 receptors but has no effect on the decrease of cAMP levels induced by THC in CHO cells transfected with the human CB1 receptors.

Furthermore, 3Bn17MeP in vitro is more selective than its endogenous counterpart pregnenolone. Indeed, pregnenolone (10 μM) displaces the binding (>80%) of the progesterone, glucocorticoid and androgen receptors, as well as the binding of the benzodiazepine receptors (>40%). 3Bn17MeP (10 μM) does not modify the binding of these receptors or of any of the other receptors (85 in total) that were studied using the CEREP high-throughput profile.

Example 3

Efficacy of 3Bn17MeP in Preclinical Models of Cognitive Disorders

The preclinical evaluation of 3Bn17MeP efficacy in cognitive disorders can be conducted on preclinical models associated with cognitive disorders, including on available animal models of neurodevelopmental disorders (e.g. Down syndrome and Fragile X syndrome), neurocognitive disorders (e.g. Alzheimer disease, Parkinson disease) and of age-related cognitive decline.

Mouse models of Down syndrome, Fragile X syndrome and age-related cognitive decline have been selected because:

Down syndrome is the most common genetic birth defect in human and is characterized by marked intellectual disabilities (Grieco et al., 2015).

Fragile X syndrome is the main monogenic cause of intellectual disability and autism (Hunter et al., 2014).

The Ts65Dn and the fmr1-KO mouse lines, the mouse models of Down syndrome and Fragile X syndrome, respectively, are the most widely used preclinical models of neurodevelopmental disorders (Chang et al., 2013).

Aging is the highest risk factor associated with neurocognitive disorders and, in particular, with neurodegenerative diseases such as Alzheimer disease (DSM-5™). Hence, age-related cognitive impairments are often the premises of pathological cognitive decline.

The enhancing effect of 3Bn17MeP administration was studied on three cognitive functions, recognition memory, declarative/relational memory and working memory.

Recognition refers to type of memory retrieval occurring when a previously experienced event matches to the stored memory of this event.

Declarative/relational memory: in human, declarative memory is a type of long-term memory referring to the intentional recollection of information, previous experiences and concepts. One property of declarative memory is the capacity of making relationships between spatially and/or temporally distinct elements of experience (Sellami et al., 2017). Indeed, declarative/relational memory is flexible, allowing to recall and manipulate two pieces of information acquired separately to make inferences or to guide a decision.

Working memory is a type of executive function allowing to temporarily store and process information. It is required to carry out everyday life activities such as holding a conversation, reasoning, reading comprehension.

These processes are cardinal for normal cognitive functioning and their impairments are probably the most incapacitating cognitive symptoms. For instance, acquisition of language requires to recognize and remember words, and to process with their meaning to understand and make oneself understood. Moreover, impairments of these processes are commonly detected in diseases causing cognitive disorders and are reproduced in preclinical models of these diseases including Ts65Dn mice, fmr1-KO mice and aged mice.

Thus, the following studies have been performed to evaluate the efficacy of 3Bn17MeP in cognitive disorders;

a. Object recognition impairment associated with Down syndrome;
b. Declarative/relational memory impairment associated with Down syndrome;
c. Working memory impairment associated with Down syndrome;
d. Object recognition impairment associated with Fragile X syndrome;

Long-term relational/declarative memory impairment associated with ageing

In the following preclinical studies, 3Bn17MeP has been administered by the oral route in two different formulations that can be safely used in humans.

3Bn17MeP can be solubilized in corn oil, a long chain triglyceride vegetable oil. This lipid formulation has been administered per os by gavage as a liquid.

3Bn17MeP can be dissolved in tap water containing 0.3% of 2-Hydroxypropyl-β-cyclodextrin (HP-β-CD). This solution has been administered orally to mice as daily ad libitum beverage in a glass bottle. Tap water containing 0.3% HP-β-CD was used as control vehicle. During 3Bn17MeP administration, bottles were weighed 3 times a week to monitor 3Bn17MeP intake. The volume of solution consumed daily per mouse was approximately 4 ml. For example, a concentration of 3Bn17MeP at 0.6 μg/ml in drinking water, corresponds to approximately 80 μg/kg in a mouse weighing 30 g.

The preclinical models used to evaluate the efficacy of 3Bn17MeP are described as follows:

Preclinical model of Down syndrome: Ts65Dn mice are characterized by the triplication of chromosome 16 which contains the majority of orthologous to human chromosome 21 genes (Gardiner, 2015). Ts65Dn mice well recapitulate the cognitive impairments observed in Down syndrome and is the most studied preclinical model of Down syndrome (Gardiner, 2015). Experimental mice derive from the breeding of TS65Dn females (B6EiC3Sn.BLiA-Ts(1716)65Dn/DnJ; Jackson Laboratory; Stock No: 5252) with males B6EiC3Sn.BLiAF1 (Jackson Laboratory; Stock No: 3647). Transgenic mice (Ts65Dn) and their wild type (WT) littermates are from a mixed DBA/2J×C57B1/6J×C3H/HeJ background.

Preclinical model of Fragile X syndrome: fmr1-KO mice are characterized by the targeted deletion of exon 5 of the fmr1 gene sequence (Kazdoba et al., 2014). This deletion results in silencing fmr1 gene and thus suppression of the encoded protein, the fragile X mental retardation protein (FMRP). The main role of FMRP is to regulate local protein synthesis in neurons by limiting mRNA translation. The loss of FMRP leads to impairment of neuronal maturation that is associated with sensorimotor, behavioral and cognitive defects (Kazdoba et al., 2014). In particular, fmr1-KO mice express long term memory impairment including object recognition impairment (Busquets-Garcia et al., 2013). Experimental mice derive from the breeding of fmr1-KO mice (FVB.129P2-Pde6b+ Tyrc-ch Fmr1tm1Cgr/J line; The Jackson Laboratory, Stock No: 4624) with wild-type mice (WT; FVB.129P2-Pde6b+ Tyrc-ch/AntJ; The Jackson Laboratory, Stock No: 4828). Transgenic mice and their wild-type littermates are from an FVB background.

Preclinical model of age-related cognitive decline: 19 to 22-month-old C57B1/6J mice are known to express cognitive deficits as compared to 3-4-month-old young adults C57B1/6J mice bred in the same conditions (Sellami et al., 2017).

Example 3a

Efficacy of 3Bn17MeP on Object Recognition Impairment Associated with Down Syndrome In mice the object recognition test, of which exist several variants, is based on spontaneous novelty preference. Accordingly, mice explore longer novel objects (Ennaceur, 2010) and show "recognition" of an object that they have already encountered by exploring it less. The memory of one specific object can be evaluated after a short delay (e.g. few minutes to one hour) or a long delay (e.g. 24 hours).

The aim of these studies is to evaluate the effect of 3Bn17MeP administration on object-recognition impairment in Ts65Dn mice, a preclinical model of Down syndrome.

In a first study (FIG. 6A), short-term object recognition was tested using a sequential procedure in which objects were presented one at a time. Recognition of a previously encountered object thus manifested by a reduction of exploration of this object. This procedure was chosen because it is the closest to the object recognition tasks used in human (e.g. Cantab Pattern Recognition Memory) and in which Down syndrome subjects have been shown to be impaired. In this task objects/patterns were presented successively, and recognition was evaluated after a delay of few minutes (Edgin et al., 2012).

In a second study (FIG. 6B), long-term object recognition was tested. Although long-term memory is not one of the major impairments observed in Down syndrome subjects, this test is the one that has been used to demonstrate an effect of CB1 orthosteric antagonists on cognitive performance. For this reason, it was important to analyze the effects of 3Bn17MeP on this specific task.

Materials and Methods

Effect of 3Bn17MeP on Short-Term Sequential Object Recognition in a Preclinical Model of Down Syndrome Mice were allowed to explore 3 different objects (A, B, C) presented one after the other and following one of the two possible sequences: A-C-C-B-A and A-B-C-C-A. In an open field, mice were exposed to object A for 5 min and then placed back into their home cage. After a delay of 5 minutes, mice were exposed to object B or C for 5 min and then placed back into their home cage, and so on. Consequently, the retention delay between two presentations of object C was of 5 minutes whereas the retention delay between two presentations of object A was of 35 minutes. The time spent exploring object A or C at the first presentation was compared with the time exploring the same object at the second presentation. This parameter is used to evaluate object recognition performances.

3Bn17MeP (0.6 μg/ml in 0.3% HP-β-CD) or vehicle (0.3% HP-β-CD) were administered orally ad libitum as daily beverage. Male and female Ts65Dn and WT mice (3 to 4-month-old; n=7-11 per group) were given free access to vehicle or 3Bn17MeP solution. Before the object recognition procedure, mice were tested in the radial maze. Object recognition was performed after 2 months of 3Bn17MeP or vehicle administration.

Effect of 3Bn17MeP on Long-Term Object Recognition in a Preclinical Model of Down Syndrome In mice long term memory can be evaluated using the object recognition test in which the memory of one specific object is evaluated 24 h later. Mice were allowed to explore 2 identical objects in an "L"-shaped maze. The day after, object recognition was tested by replacing one object by a novel one. According to the spontaneous novelty preference, mice explore longer novel objects (Ennaceur, 2010). The ratio between the time spent exploring the novel and the familiar objects is used as an index of discrimination between familiarity and novelty. Therefore, this parameter is used to evaluate object recognition performances.

The effect of repeated per os administrations of 3Bn17MeP at 15 μg/kg in corn oil or vehicle (corn oil; 2 ml/kg) was studied in 2 to 4-month-old Ts65Dn and WT male mice (n=7-8 per group). 3Bn17MeP was administered twice a day (at 9 am and 5 pm) for 7 consecutive days. Object recognition test was performed at the $7^{th}$ day, 3 hours after the $13^{th}$ 3Bn17MeP or vehicle administration.

Results

In the short-term sequential object recognition protocol (FIG. 6A), wild-type mice were able to recognize the objects already encountered as shown by a decreased exploration time between the first and the second presentation of the same object, and this after both 5- and 35-min delays between presentations. In contrast, Ts65Dn mice receiving vehicle did not show a significant decrease in exploration time between consecutive presentations, independently from the delay, indicating that Ts65Dn were impaired in short-term object recognition. Ts65Dn administered with 3Bn17MeP (0.6 μg/ml) explored significantly less the familiar object after 5 and 35 minutes, acquiring a performance similar to the one of wild-type animals.

Figure 6:
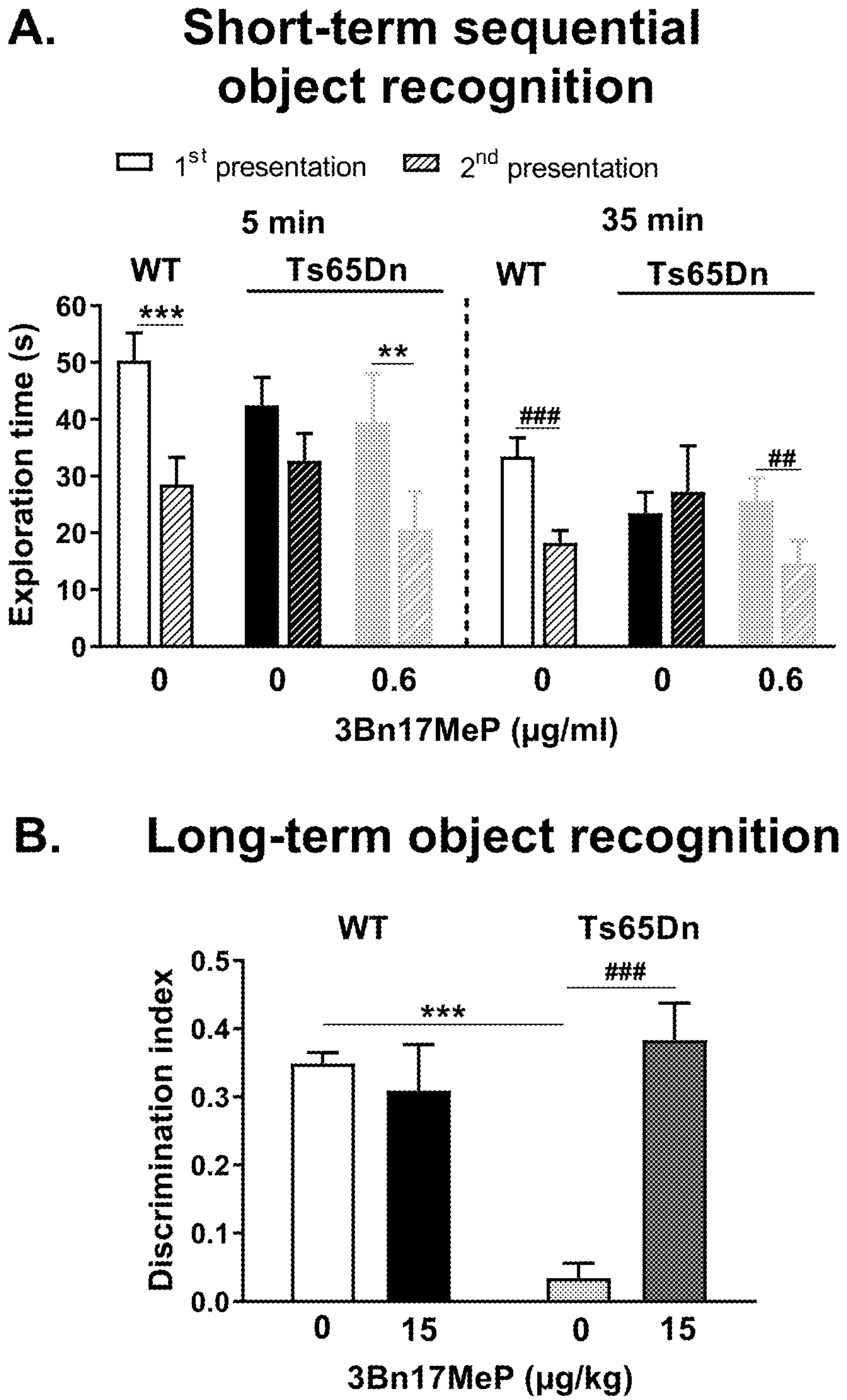
FIG. 6: Effect of 3Bn17MeP on object recognition impairment in a preclinical model of Down syndrome.

In the long-term object recognition protocol (FIG. 6B), Ts65Dn administered with corn oil vehicle exhibit a profound object recognition impairment as compared to WT (FIG. 6B). Administration of 3Bn17MeP (15 μg/kg) enhanced the discrimination index of Ts65Dn mice at the level of WT.

Thus, 3Bn17MeP restored full object recognition abilities in this preclinical model of Down syndrome.

Example 3b

Efficacy of 3Bn17MeP on Declarative/Relational Memory Impairment Associated with Down Syndrome The aim of this study is to evaluate the effect of 3Bn17MeP administration on declarative/relational memory impairment in Ts65Dn mice, a model of Down syndrome. The following declarative/relational memory test has been performed in a radial maze procedure that have been successfully employed to detect impairments both in patients with Down syndrome (in a virtual radial maze) and in Ts65Dn mice (in a radial maze) using a very similar protocol.

Materials and Methods

The relational memory task was performed using 8-arm radial mazes. The diameter of the central platform was 30 cm and the arms were 55 cm length; 10 cm width and 100 cm height from the floor. Each arm was equipped with a retractable door at its entrance and with a food-pellet delivering system at its end. Each maze was placed in a room containing visual cues on the walls to enable spatial discrimination. There was no intra-maze cue. Each maze was fully automated by videotracking (IMETRONIC Pessac—France). This allowed to automatically control the doors of the arms (opening/closure) and food delivery according to the location of the mouse.

Food-restricted mice (85% of their original body weight all throughout the study) were first submitted to 3 sessions of habituation to the mazes. During each habituation session, the mouse freely explored the maze until it visited each of the 8 arms, or 30 min elapsed. At the beginning of each habituation session, the mouse was placed in the central platform with all the arms closed. After one minute, all the arms were baited with food reward (pearl of dry pasta, Panzani “Pâtes Perles”, 100% durum wheat, approximately 10 mg each) and opened simultaneously. An arm was considered as visited as soon as the mouse reached the food tray at its end. The door of the visited arm closed after the mouse was back in the center.

Mice were submitted to one daily session of habituation. At the end of the second session, if a mouse failed to visit all the arms within the allocated time or to collect the food rewards of the four last visited arms, they were submitted to an additional session the same day and another the following day if this criterion was not reached. If after the third day of habituation a mouse still failed to explore all the arms or to collect the rewards of the four last visited arms, it was excluded from the experiments.

Acquisition began 24 h after the last habituation session. The acquisition stage consisted in learning the positions of the food pellets within the maze. The position of the reward did not change throughout the whole procedure. Six arms out of eight were used (3 pairs (A, B or C) of adjacent arms). One arm of each pair contained reward at its end, the other arm of each pair was not baited.

At the beginning of each daily session, the mouse was placed at the center of the maze with no access to the arms. The doors of the first pair of arms then opened giving access to both arms of the pair. Once the mouse had visited one arm and went back to the central platform, the door closed, and the animal was confined in the central platform. Two doors open again giving access to a pair of arms immediately after (0-sec inter-trial interval). Once the animal had visited one of the arms and returned to the central platform the doors closed again before the next trial. Within each session, the mouse was submitted to 20 repeated and successive presentations of the 3 pairs of arms, one at a time.

The number of correct responses was measured at each session. A mouse was considered to have acquired the test when it reached a learning criterion. This criterion consisted in at least (i) 75% of correct responses (for the three pairs) over two consecutive sessions and (ii) 62% of correct responses for each of the 3 pairs over two consecutive sessions.

The flexibility test began the day after learning criterion was reached. Indeed, mice could perform the flexibility test at different days.

In this flexibility task, a novel pair was formed by recombining 2 arms from two different pairs acquired during the acquisition stage. The position of the food in the maze did not change, but the way of presenting the arms changed. Indeed, instead of pairs A and B, a pair so called AB was presented to the mouse. The pair AB consisted in the combination of the two adjacent arms of pairs A and B (i.e. one arm baited and the other non-baited). This pair represented the test trial of the flexibility test. The dependent variable measuring flexibility (i.e. declarative/relational memory) performance is the percentage of correct responses at presentation of the pair AB.

3Bn17MeP (0.6 μg/ml in 0.3% HP-β-CD) or vehicle (0.3% HP-β-CD) was administered orally ad libitum as daily beverage. Male and female Ts65Dn and WT mice (3 to 4-month-old; n=7 per group) were given free access to vehicle or 3Bn17MeP solution (0.6 μg/ml) 7 days before the start of the radial maze procedure and until the end of the study. At the end of the behavioral study, mice were sacrificed, blood and brain samples were collected. 3Bn17MeP was quantified by LC/MS-MS chromatography in both plasma and brain.

Results

Figure 7:
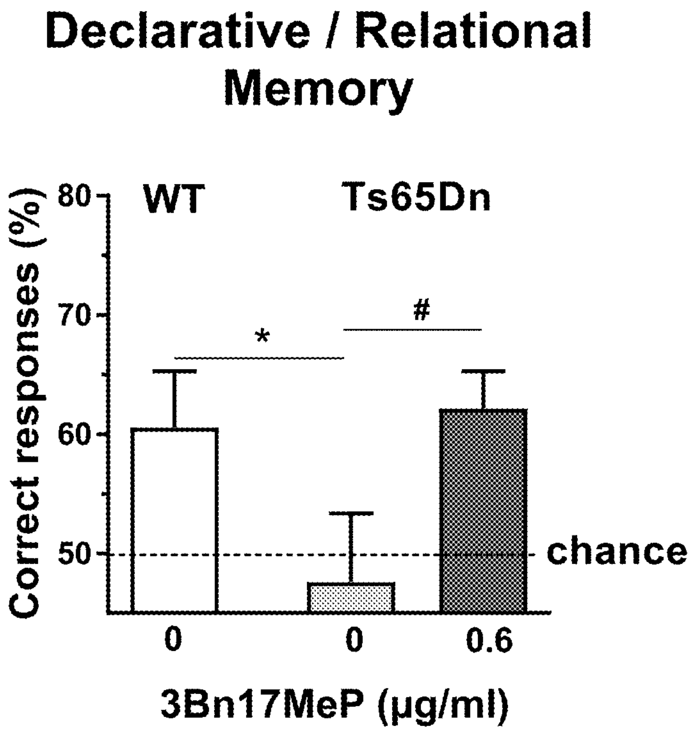
FIG. 7: Effect of 3Bn17MeP on declarative/relational memory impairment in a preclinical model of Down syndrome. Chronic oral administration of 3Bn17MeP in drinking water (0.6 μg/ml) in Ts65Dn mice restores memory performance (as measured by correct response percentage) at the level of WT mice. The dotted line depicts chance level. *p<0.05, WT vs Ts65Dn administered with the vehicle of 3Bn17MeP (0 μg/ml; unpaired t-test). #p<0.05, vehicle of 3Bn17MeP (0 μg/ml) vs 3Bn17MeP (0.6 μg/ml) in Ts65Dn (unpaired t-test). No significant effect between WT and Ts65Dn administered with 3Bn17MeP (0.6 μg/ml; unpaired t-test).

In the flexibility test, Ts65Dn mice administered with vehicle were impaired as compared to WT. The choice accuracy of vehicle-treated Ts65Dn mice was not above chance level (FIG. 7). Administration of 3Bn17MeP (0.6 μg/ml) enhanced choice accuracy of Ts65Dn mice that reached the level of WT. Thus, in this preclinical model of Down syndrome 3Bn17MeP entirely restores the flexibility of learning, this function underlying correct declarative/relational memory abilities.

3Bn17MeP accesses to both the brain and plasma of the Ts65Dn mice. The mean plasma and brain concentrations of 3Bn17MeP were respectively 1.33 ng/ml and 5.91 ng/g which gives a brain/plasma ratio of 4.4.

Example 3c

Efficacy of 3Bn17MeP on Working Memory Impairment Associated with Down Syndrome

The aim of this study is to evaluate the effect of 3Bn17MeP administration on working memory impairment in Ts65Dn mice, a model of Down syndrome. The following working memory test has been performed in a radial maze procedure that have been successfully employed to detect impairments both in patients with Down syndrome (in a virtual radial maze) and in Ts65Dn mice (in a radial maze) using a very similar protocol.

Materials and Methods

The working memory task was performed using 8-arm radial mazes described in Example 3a. Food restriction and habituation procedure were performed as described in Example 3a. The working memory procedure began 24 h after the last habituation session. Each mouse was submitted to 15 daily learning sessions (5 blocks of 3 days) made of 23 trials each. Six arms out of eight were used during the working memory test (3 pairs (A, B or C) of adjacent arms).

At the beginning of each daily session, the mouse was placed at the center of the maze with no access to the arms. The doors of the first pair of arms then opened giving access to both arms of the pair. Once the mouse had visited one of the arms and goes back to the central platform, the door closed, and the animal was confined in the central platform for 10 sec (inter-trial interval, ITI) before two doors opened again giving access to a pair of arms. Once the animal had visited one of the arms and returns to the central platform the doors close again for 10 sec before the next trial. Within each session, the mouse was submitted to repeated and successive presentations of the 3 pairs of arms one at a time. At the first presentation of each arm pair the food reward was present in both arms. At subsequent presentations of arm pairs, the food reward was only present in the arm opposite to the one that was previously visited, independently of the correctness of the previous response. The dependent variable measuring working memory performance is the percentage of correct responses at each bloc of three sessions.

3Bn17MeP (0.06 μg/ml in 0.3% HP-β-CD) or vehicle (0.3% HP-β-CD) was administered orally ad libitum as daily beverage. Male and female Ts65Dn and WT mice (3 to 4-month-old; n=24-26 per group) were given free access to vehicle or 3Bn17MeP solution (0.06 μg/ml) 7 days before the start of the radial maze procedure and until the end of the study.

Results

Figure 8:
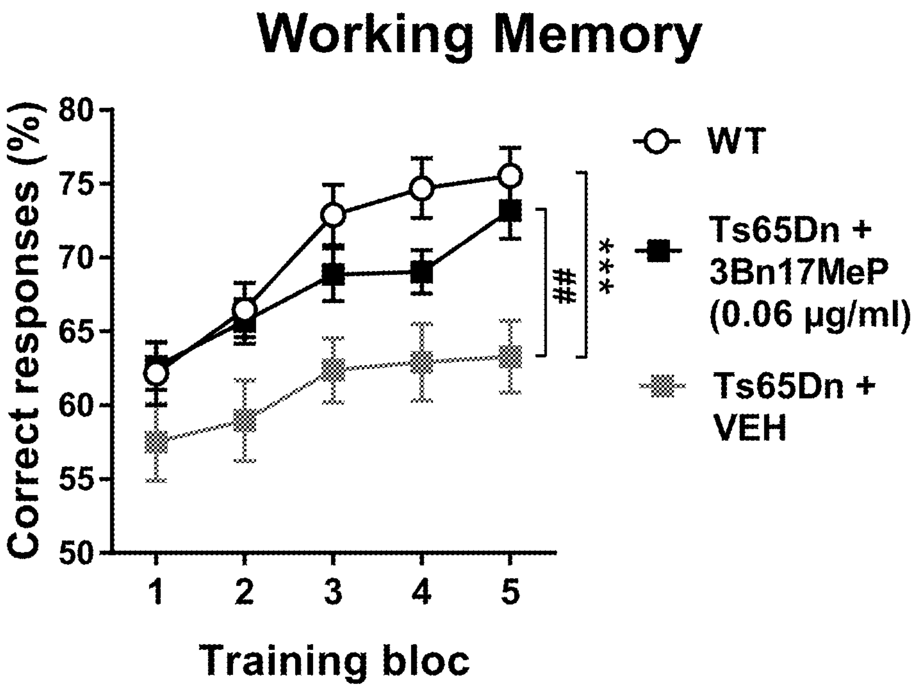
FIG. 8: Effect of 3Bn17MeP on working memory impairment in a preclinical model of Down syndrome. Chronic oral administration of 3Bn17MeP in drinking water (0.06 μg/ml) in Ts65Dn mice restores memory performance (as measured by correct response percentage) at the level of WT mice. ***p<0.001, WT vs Ts65Dn administered with the vehicle of 3Bn17MeP (VEH; Tukey test). ##p<0.01, VEH vs 3Bn17MeP (0.06 μg/ml) in Ts65Dn (Tukey test). No significant effect between WT and Ts65Dn administered with 3Bn17MeP (0.06 μg/ml; Tukey test).

The percentage of correct responses was strongly decreased in Ts65Dn mice administered with vehicle as compared to WT (FIG. 8). Administration of 3Bn17MeP (0.06 μg/ml) increased correct responses in Ts65Dn as compared to vehicle mice that reached the level of WT at the end of the working memory procedure. Thus, 3Bn17MeP corrects working memory impairment in this preclinical model of Down syndrome.

Example 3d

Efficacy of 3Bn17MeP on Object Recognition Impairment Associated with Fragile X Syndrome The aim of this study is to evaluate the effect of 3Bn17MeP administration on object-recognition impairment in fmr1-KO mice, a preclinical model of Fragile X syndrome.

Materials and Methods

The object recognition procedure was performed as described in Example 3a.

The effect of repeated per os administrations of 3Bn17MeP at 15 μg/kg in corn oil or vehicle (corn oil; 2 ml/kg) was studied in 2 to 4-month-old fmr1-KO and WT male mice (n=7-8 per group). 3Bn17MeP was administered twice a day (at 9 am and 5 pm) for 7 consecutive days. Object recognition test was performed at the 7$^{th}$ day, 3 hours after the 13th administration of 3Bn17MeP or vehicle.

Results

Figure 9:
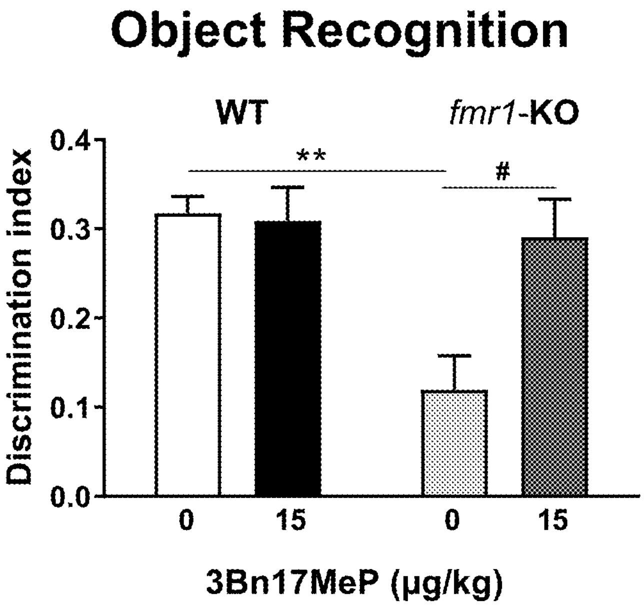
FIG. 9: Effect of 3Bn17MeP on object recognition impairment in a preclinical model of Fragile X syndrome. Repeated per os administrations of 3Bn17MeP in corn oil (15 μg/kg; b.i.d) corrects the decreased discrimination index of fmr1-KO mice from WT. **p<0.01, WT vs fmr1-KO administered with the vehicle of 3Bn17MeP (0 μg/kg; Tukey's test). #p<0.05, vehicle of 3Bn17MeP (0 μg/kg) vs 3Bn17MeP (15 μg/kg) in fmr1-KO (Tukey's test). No significant effect between WT and fmr1-KO administered with 3Bn17MeP (15 μg/kg; Tukey's test).

Fmr1-KO administered with corn oil vehicle exhibit object recognition impairment as compared to WT (FIG. 9). Administration of 3Bn17MeP (15 μg/kg) enhanced the discrimination index of fmr1-KO mice at the level of WT. Thus, 3Bn17MeP restored full object recognition abilities in this preclinical model of Fragile X.

Example 3e

Efficacy of 3Bn17MeP on Long-Term Relational/Declarative Memory Impairment Associated with Ageing The following cognitive test has been successfully employed to detect declarative/relational memory impairments both in human elderly subjects (in a virtual radial maze) and in aged mice (in a radial maze) using a very similar procedure (Sellami et al., 2017). Indeed, both aged human subjects and aged mice are impaired when the flexibility test require to recall and manipulate two pieces of information acquired within two distinct temporal sequences.

Materials and Methods

The relational memory task was performed using 8-arm radial mazes described in Example 3b. Food restriction and habituation procedures were performed as described in Example 3b. Acquisition began 24 h after the last habituation session. The acquisition stage consisted in learning the positions of the food pellets within the maze. The position of the reward did not change throughout the whole procedure. One arm of each pair contained reward at its end, the other arm of each pair was not baited.

Acquisition is based on a go-no go procedure. The arms are presented one by one. Subjects are expected to visit the rewarded arms faster than the non-rewarded arms. At the beginning of each daily session, the mouse was placed at the center of the maze with no access to the arms. The doors of the first arm then opened. Once the mouse had visited the arm and went back to the central platform (or after a delay of 90 s if it did not visit the arm), the door closed and the animal was confined in the central platform. The door of an arm then open immediately after (0-sec inter-trial interval). Once the animal had visited the arm and returned to the central platform (or after a delay of 90 s if it did not visit the arm) the door closed again before the next trial. Each daily session contained 40 successive arm presentations (i.e. trials) organized into two distinct temporal sequences. In the first sequence (20 trials), four arms of the maze were presented alternatively (two baited and two non-baited). Consecutively, the second sequence started (20 trials); the four other arms of the maze were presented alternatively (two baited and two non-baited). The arms are presented in their respective sequence during all the acquisition phase.

At each trial, the latency to visit the arm is measured. A mouse was considered to have acquired the test when it reached a learning criterion. This criterion consisted in (i) at least 50% less time to visit the rewarded arms as compared to non-rewarded arms, averaged on two consecutive sessions and (ii) at least 30% less time to visit the rewarded arms averaged on the last session.

The flexibility test began the day after learning criterion was reached. Indeed, mice could perform the flexibility test at different days.

Flexibility of learning was evaluated in the following conditions. The eight arms of the maze were virtually divided in pairs each made of two adjacent arms, one rewarded and one non-rewarded. Pairs consisted in one arm acquired in the first sequence and the other acquired in the second sequence. The position of the food in the maze did not change, but the way of presenting the arms changed. At the beginning of the flexibility session, the mouse was placed at the center of the maze with no access to the arms. The doors of the first pair of arms then opened giving access to both arms of the pair. Once the mouse had visited one arm and went back to the central platform, the door closed and the animal was confined in the central platform. Two doors open again giving access to a pair of arms immediately after (0-sec inter-trial interval). Once the animal had visited one of the arms and returned to the central platform the doors closed again before the next trial. The mouse was submitted to 20 repeated and successive presentations of the pairs, one at a time.

The percentage of correct responses for each pair was measured. Choice accuracy for the pairs made of arms that were presented in different sequences reflected the relational memory performance.

3Bn17MeP (0.6 μg/ml in 0.3% HP-β-CD) or vehicle (0.3% HP-β-CD) was administered orally ad libitum as daily beverage. 19 to 22-month-old male C57B1/6J mice (n=9-12 per group) were given free access to vehicle or 3Bn17MeP solution (0.6 μg/ml) 7 days before the start of the radial maze procedure and until the end of the study.

At the end of the behavioral study, mice were sacrificed, blood and brain samples were collected. 3Bn17MeP was quantified by LC/MS-MS chromatography in both plasma and brain.

Results

Figure 10:
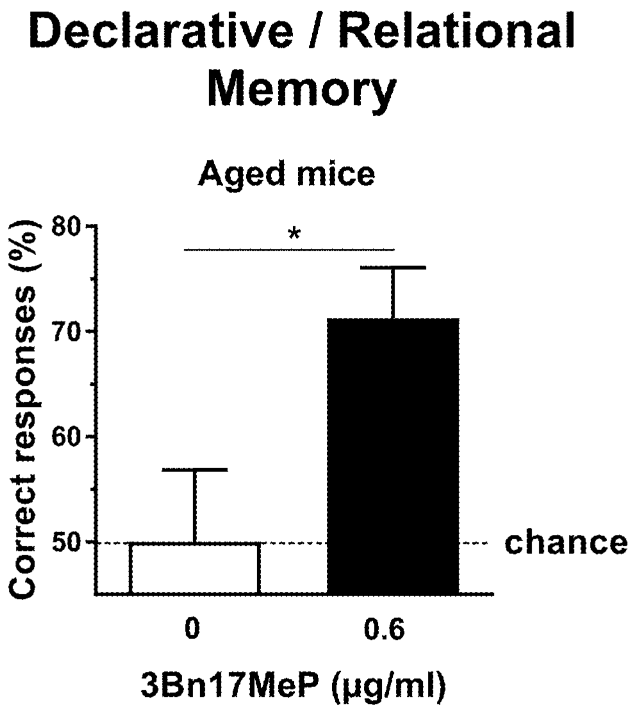
FIG. 10: Effect of 3Bn17MeP on declarative/relational memory impairment in a preclinical model of age-related cognitive impairments. Chronic oral administration of 3Bn17MeP in drinking water (0.6 μg/ml) improves memory performance of aged mice (as measured by correct response percentage). The dotted line depicts chance level. *p<0.05, vehicle of 3Bn17MeP (0 μg/ml) vs 3Bn17MeP (0.6μg/ml; unpaired t-test).

In the flexibility test, the choice accuracy of vehicle-treated aged mice was not above chance level (50%, FIG. 10). Administration of 3Bn17MeP (0.6 μg/ml) strongly enhanced choice accuracy of aged mice that reached more than 70% of correct responses. Thus, 3Bn17MeP restores relational memory ability in aged mice.

3Bn17MeP accesses to both the brain and plasma of the aged mice. The mean plasma and brain concentrations of 3Bn17MeP were respectively 1.28 ng/ml and 6.75 ng/g which gives a brain/plasma ratio of 5.3.

Conclusion

The compound of the present invention shows in vivo a very high potency in correcting a large spectrum of cognitive impairments including long-term declarative/relational memory, recognition and executive functions impairments. 3Bn17MeP shows efficacy in several models of cognitive disorders including Down syndrome, Fragile X syndrome and age-related cognitive decline. Therefore, 3Bn17MeP benefits from a wide spectrum of actions on the cognitive function and is thus likely a global cognitive enhancer.

Example 4

3Bn17MeP has None of the Behavioral Side Effects of Orthosteric CB1 Antagonists The pharmacological profile and the effects of 3Bn17MeP on phenotypes related to adverse effects of the orthosteric CB1 antagonist rimonabant were evaluated. Orthosteric CB1 antagonists such as Acomplia® were withdrawn from the market because of adverse effects. Consequently, for a therapeutic tool inhibiting the CB1 to be of practical use in humans it should not have the known adverse effects of orthosteric CB1 antagonists.

Known adverse effects of orthosteric antagonists of the CB1 receptors and in particular of rimonabant are: 1. A reduction of food intake and body weight that is a sign of a non-specific effect on reward pathways; 2. A induction of anxiety- and depression-related behavior. Therefore, the effects 3Bn17MeP on food intake, body weight and on anxiety- and depression-related behaviors in mice were compared to those of the orthosteric CB1 antagonist rimonabant.

Rimonabant is known to induce alterations in spontaneous behaviors in rodents such as scratching, hyperactivity followed by sedation and convulsions at doses that are 6 times the therapeutic dose for the treatment of obesity (Zavatti et al., 2011; EPAR discussion, EMEA 2006). Indeed, the effect of 3Bn17MeP on spontaneous behaviors has been studies in mice.

Example 4a

Absence of Undesired Effects Induced by 3Bn17MeP on Food Intake and Body Weight as Compared to Rimonabant in Wild-Type Mice These experiments aimed to evaluate the ability of an acute treatment with 3Bn17MeP to decrease food intake in lean mice ad libitum fed with standard laboratory chow and to compare these potential effects with those of the orthosteric CB1 antagonist rimonabant. Food intake and body weight were studied because decreases in food intake and body weight is a prototypical consequence of CB1 orthosteric antagonists both in mice and in humans (Carai et al., 2006).

Materials and Methods

Effects of an Acute Administration of 3Bn17MeP on Food Intake in Lean Mice Ad Libitum Fed with Standard Chow Spontaneous intake of standard chow in mice was evaluated during the dark phase of the light-dark cycle. The amount of food eaten was measured at light-off, 3 hours and 13 hours after light-off.

The effect of an acute administration of 3Bn17MeP (0.05, 5, 15 and 30 mg/kg, per os in corn oil, 5 ml/kg) or vehicle (corn oil) on food intake was compared to the one of rimonabant (10 mg/kg, ip in 0.9% NaCl containing 2% DMSO and 2% Tween80, 10 ml/kg) or vehicle (2% DMSO and 2% Tween80 in 0.9% NaCl) in male C57BL/6J mice (n=7-8 per group). 3Bn17MeP and rimonabant were administered 3 hours and 30 min before the start of the dark phase, respectively.

Effects of Repeated Administrations of 3Bn17MeP on Body Weight of Lean Mice Ad Libitum Fed with Standard Chow The effect of repeated administrations of 3Bn17MeP (0.05, 5, 15 and 30 mg/kg, per os in corn oil, 5 ml/kg) or vehicle (corn oil) on body weight was compared to the one of rimonabant (10 mg/kg, ip in 0.9% NaCl containing 2% DMSO and 2% Tween80, 10 ml/kg) or vehicle (2% DMSO and 2% Tween80 in 0.9% NaCl) in male C57BL/6J mice (n=7-8 per group). 3Bn17MeP and rimonabant were administered once a day for 40 days. Mice were weighed prior to drug administration every day at the first week of treatment and then four days per week.

Results

Figure 11:
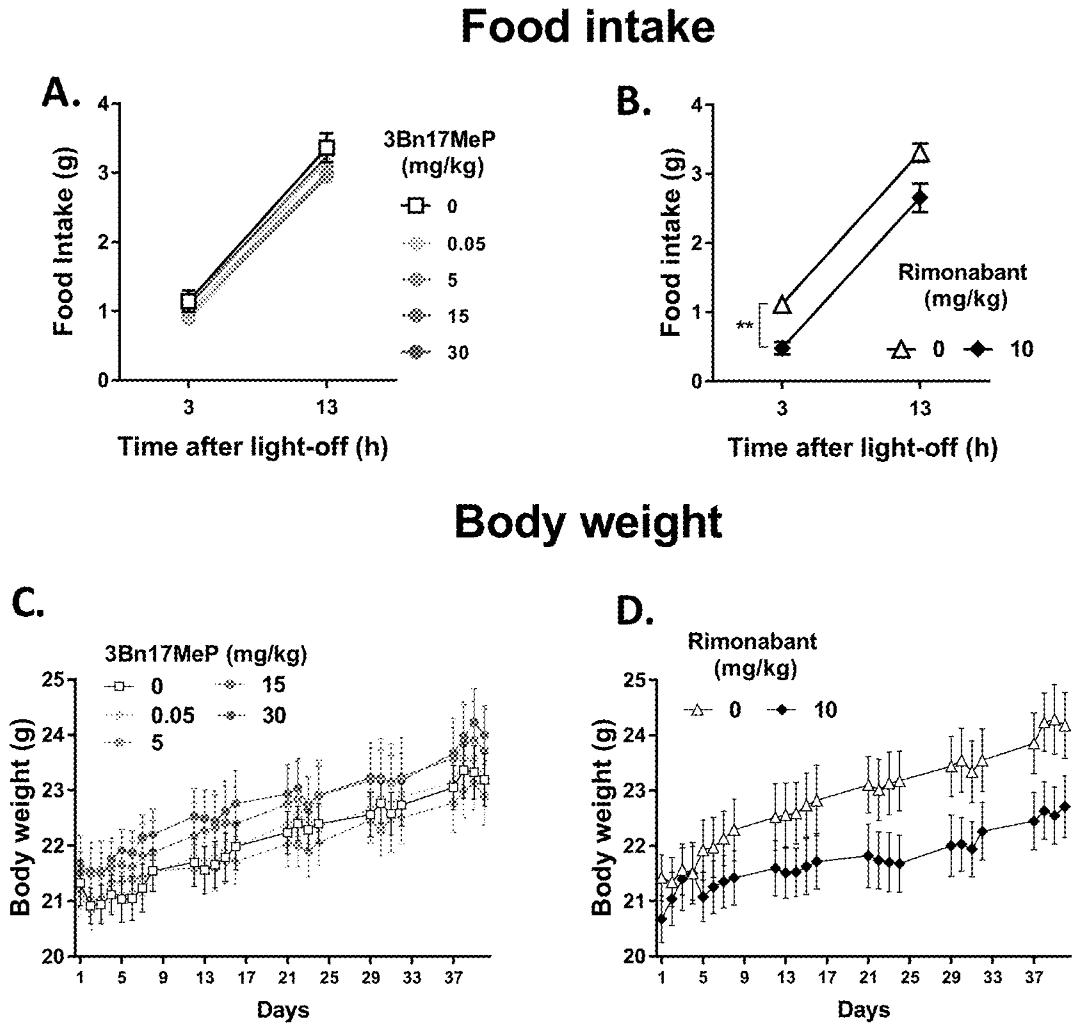
FIG. 11: Effects of repeated administrations of 3Bn17MeP and of rimonabant on food intake and body weight in wild-type mice.

3Bn17MeP (0.05, 5; 15 and 30 mg/kg) did not modify food intake as compared to vehicle (FIG. 11A), whilst rimonabant (10 mg/kg) significantly decreased food intake during the first 3 hours after light-off (FIG. 11B). At the same doses 3Bn17MeP did not modify body weight evolution during the 40 days of repeated administration as compared to vehicle (FIG. 11C). Conversely, rimonabant (10 mg/kg) decreased body weight of the mice during this period (FIG. 11D).

Example 4b

Absence of Undesired Effects Induced by 3Bn17MeP on Anxiety- and Depressive-Like Behaviors as Compared to Rimonabant in Wild-Type Mice Anxiety and depression-related behaviors were studied because increases in anxiety and depression are consequences of repeated treatment with CB1 orthosteric antagonists both in rodents and in humans (Bellocchio et al., 2013; Moreira et al., 2009). Anxiety-like behaviors were studied in the elevated plus maze (EPM) because this model is widely used in rodents to evaluate the putative anxiogenic or anxiolytic effects of pharmacological compounds (Walf and Frye, 2007). Depression-related behaviors were studied using the sucrose preference test that is largely used as a model of anhedonia, one of the cardinal symptoms of depression (Overstreet, 2012).

The aim of these experiments was to evaluate the effects of a repeated treatment with 3Bn17MeP on depression- and on anxiety-related behaviors in mice. These effects were compared to those of the orthosteric CB1 receptor antagonist rimonabant, known to induce depression- and anxiety-like behaviors both in mice and in humans.

Materials and Methods

Anxiety-Like Behaviors in the Elevated Plus Maze

The EPM apparatus was made of grey polyvinyl chloride and consisted of four elevated arms. The arms (height, 60 cm; length, 37 cm; width, 6 cm; each) were arranged in a cross-like disposition, with two opposite arms being enclosed by walls and the two other arms being open. A video camera placed on the top of the maze and connected to a tracking system allowed the automatic scoring of the locomotion of the mice in the maze. The light intensity of the maze was set at 45 lux in the open arms. One mouse was placed in the center of the EPM and was then free to explore the entire maze for 5 minutes. The time spent and the number of entries into the open arms and closed arms were measured. A decrease in the percentages of visits and/or of the time spent in open arms reflects an increase in anxiety levels.

The effect of acute per os administration of 3Bn17MeP dissolved in corn oil at 30 mg/kg or of vehicle (corn oil; 5 ml/kg) was studied in the EPM test in 2-month-old male C57B1/6J mice (n=10 per group). The EPM test was performed 3 hours after 3Bn17MeP administration. Rimonabant was dissolved in a vehicle containing DMSO, (2%), Tween80 (2%) in injectable NaCl 0.9%. Within the same study, the effect of intraperitoneal injection of rimonabant at 10 mg/kg or of vehicle alone (10 ml/kg) was studied in the EPM in 2-month-old male C57B1/6J mice (n=10 per group). The EPM test was performed 30 minutes after rimonabant injection.

Depressive-Like Behaviors in the Sucrose Preference Test

Sucrose preference was tested in the home cages of the mice. A sucrose solution containing 2% of sucrose (D(+) saccharose) in tap water was poured in plastic graduated bottles (volume in each bottle, 45 ml). Identical bottles were filled with tap water. All the mice were first habituated to the bottles and to the sucrose solution. One bottle containing water and one bottle containing sucrose were placed in the hopper of each home cage. To ensure that animals did not display a drinking side preference, half of the bottles containing each solution were placed on the left side of the hopper and the other half on the right side. The mice had access to the solutions from the beginning of the dark phase, at the daily peak of food and water consumption (from 7 pm to 8.30 am). The sucrose preference test was performed seven days later. Water and sucrose solutions were presented as described for habituation except that mice had access to the solutions from 12 pm to 10 pm. At each time point, the bottles were weighed, 1 g corresponding to 1 ml. The intake volume was calculated by subtracting the initial bottle weight to the final bottle weight.

The effect of repeated per os administrations of 3Bn17MeP dissolved in corn oil at 0.05; 5;

15 or 30 mg/kg or of vehicle (corn oil; 5 ml/kg) was studied in the sucrose preference test in 2-month-old male C57B1/6J mice (n=7-8 per group). Rimonabant was dissolved in a vehicle containing dimethylsulfoxide (DMSO, 2%), Tween80 (2%) in injectable NaCl 0.9%. Within the same study, the effect of repeated intraperitoneal injections of rimonabant at 10 mg/kg or of vehicle alone (10 ml/kg) was studied in the sucrose preference test in 2-month-old male C57B1/6J mice (n=8 per group). 3Bn17MeP and rimonabant were administered once a day for 28 days. The sucrose preference test was performed the $28^{th}$ day, sucrose and water solutions were delivered 3 hours after 3Bn17MeP administration and 30 min after rimonabant administration.

Results

Figure 12:
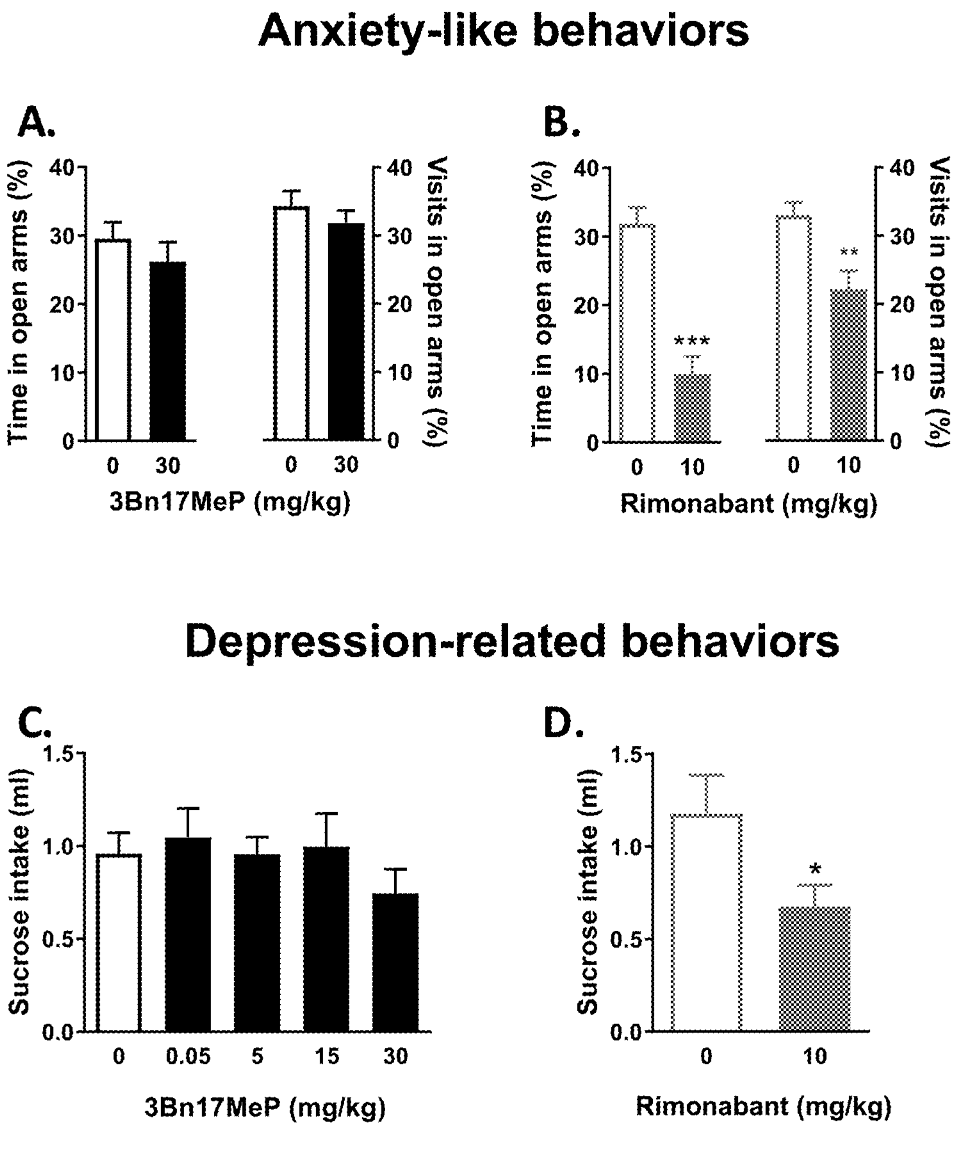
FIG. 12: Effects of 3Bn17MeP and of rimonabant on anxiety- and depression-related behaviors in wild-type mice.

3Bn17MeP, administered at 30 mg/kg acutely, had no effect on the percentage of time spent and on the percentage of visits in the open arms of the elevated plus maze (FIG. 12A). Conversely, rimonabant at 10 mg/kg markedly reduced the time spent and the number of visits in the open arms (FIG. 12B).

Chronic administrations of 3Bn17MeP up to 30 mg/kg had no effect on sucrose intake at any of the dose tested (0.05; 5; 15; 30 mg/kg) whereas rimonabant (10 mg/kg) reduced by half sucrose consumption in the same conditions (FIGS. 12C and D).

These results show that repeated administrations of 3Bn17MeP do not induce depression-like or anxiety-like behaviors in mice. In contrast, the CB1 receptor orthosteric antagonist rimonabant (10 mg/kg) induces anhedonia in the sucrose preference test and increases anxiety-like behaviors in the elevated plus maze. These results are in line with previous studies reporting similar effects of rimonabant in rodents at doses as low as 1 mg/kg (Beyer et al., 2010; Patel and Hillard, 2006).

Example 4c

3Bn17MeP Has No Effect on Spontaneous Behaviors in Mice

3Bn17MeP had no detectable effects on behaviors per se in rodents as shown by the video analysis of spontaneous behaviors in the home cage during 24 hours after per os administration of 3Bn17MeP in mice at 30 mg/kg.

Conclusion

The adverse effect of rimonabant are compared with the effects of 3Bn17MeP in TABLE 3.

TABLE 3

3Bn17MeP has none of the adverse effects of rimonabant

| IN VIVO | TEST SYSTEM | 3Bn17MeP Effect | 3Bn17MeP Highest dose tested (mg/kg) | 3Bn17MeP N fold ID100* | Rimonabant Effect | Rimonabant ID100 | Rimonabant N fold ID100** |
|---|---|---|---|---|---|---|---|
| Inhibition of food-intake and body weight (repeated administration) | male mice | No | 30 | 2000 | Yes | 10 | 1 |
| Increase in anxiety-like behaviors (acute administration) | male mice | No | 30 | 2000 | Yes | 10 | 1 |
| Increase in depression-related behaviors (repeated administration) | male mice | No | 30 | 2000 | Yes | 10 | 1 |

*Dose able to restore full object recognition abilities take as reference; i.e 15 μg/kg, per os administration in corn oil

**Reference ID100 for rimonabant effects = 10 mg/kg.

The effects of 3Bn17MeP are very different from the ones of the CB1 orthosteric antagonist rimonabant.

3Bn17MeP has none of the typical adverse effects of rimonabant and other CB1 orthosteric antagonists, such as decrease in food intake, increase in anxiety- and depression-related behaviors. This lack of effects of 3Bn17MeP was observed for all the highest doses used in each test. Moreover, 3Bn17MeP does not induce modification of spontaneous behaviors in mice. These doses of 3Bn17MeP were several times higher than the dose reversing cognitive impairments in all the models of cognitive disorder tested.

Example 5

3Bn17MeP is not Toxic In Vitro and Shows Advantageous Safety Profile In Vivo

Example 5a

In Vitro Toxicity of 3Bn17MeP

In order to study the potential in vitro toxicity of 3Bn17MeP four models were used: 1. Neurotoxicity in primary culture of rat cortical neurons. 2. Hepatotoxicity and biliary function in primary culture of rat hepatocytes in a sandwich configuration. 3. Genotoxicity measuring Histone H2AX phosphorylation (γH2AX) in HeLa cells. In these assays the effect of 3Bn17MeP was compared with the one of rimonabant. 4. Cardiotoxicity, measuring hERG current inhibition in hERG-CHO cells. 3Bn17MeP was tested up to 100 μM.

Material and Methods

Neurotoxicity

This study aimed at analyzing the cytotoxic effects of 3Bn17MeP and rimonabant in primary culture of cortical neurons. Cultured primary cortical neurons from E19 rat embryos were treated with 3Bn17MeP, rimonabant (both at 0, 10, 30 or 100 μM in NMP 0.1%) or Staurosporine (100 nM, used as a reference compound) and a soluble fluorescent cytolysis marker. Cells were then followed by time-lapse imaging during 72 hours. The cells were then permeabilized. This procedure allowed to express the cytolysis over time as a percentage of the total number of cells per well.

Genotoxicity

This study aimed at measuring Histone H2AX phosphorylation (γH2AX), which is the cellular response to DNA damage resulting in double-stranded DNA breaks. This experiment was performed in HeLa cells treated with 3Bn17MeP (0.1, 0.3, 1, 3, 10, 30 and 100 μM in NMP, 0.1%) or with rimonabant (0.1, 0.3, 1 or 100 μM in NMP, 0.1%) for 24 hours. Etoposide at 3 μM was added as positive control of genotoxic effects. An immunofluorescence was performed on treated cells with a specific antibody against the phosphorylated histone gH2AX. Nuclei were stained with a fluorescent DNA intercaling agent. The stained cells were imaged and analyzed on the BD Pathway 855 imager®.

Hepatotoxicity and Biliary Function

This study aimed at analyzing the cytotoxic effects of 3Bn17MeP in primary culture of rat hepatocytes. The percentage of cytolysed hepatocytes over time was determined by time lapse imaging with a fluorescent cytolysis marker. The number of bile canaliculi after 48 hours of treatment was determined using a fluorescent bile salt analog.

Primary rat hepatocytes from 10-12 weeks old Wistar rats were isolated using a two-step collagenase perfusion method. After 24 hours, cells were covered with a layer of Matrigel to perform a sandwich configuration culture. After 24 hours cells were treated with 3Bn17MeP or rimonabant (0, 0.1, 0.3, 1, 3, 10, 30 and 100 μM in NMP, 0.1%) and a fluorescent cytolysis marker, and then monitored by fluorescent and phase-contrast time lapse imaging for 48 hours. Cells were then stained using a fluorescent bile salt analog to measure the bile canaliculi network state and the Bsep pump activity. Acetaminophen (30 mM) and Cyclosporin A (1 μM) were added as positive controls of hepatotoxicity and biliary canaliculi loss, respectively.

Cardiotoxicity

This study aimed at measuring the effect 3Bn17MeP on the hERG channel current which is critical for the repolarization of cardiomyocytes action potentials. This experiment was performed in hERG-CHO-K1 cells treated with 3Bn17MeP (0.1, 1 and 10 μM in DMSO, 1%) for 5 min. E-4031 at 0.3 μM was added as positive control of cardiotoxic effects. hERG current was recorded by automated whole-cell patch clamp. The degree of inhibition (%) was obtained by measuring the difference between the tail current amplitudes induced by the stimulation protocol (+20 mV, 2 s and −40 mV, 1 s) applied before and after drug incubation.

Results

At none of the doses tested and in none of the tests performed, neurotoxicity (FIG. 13A), genotoxicity (FIG. 13B), hepatotoxicity (FIG. 14A), biliary functions (FIG. 14B), and cardiotoxicity, 3Bn17MeP showed toxic effect.

Figure 13:
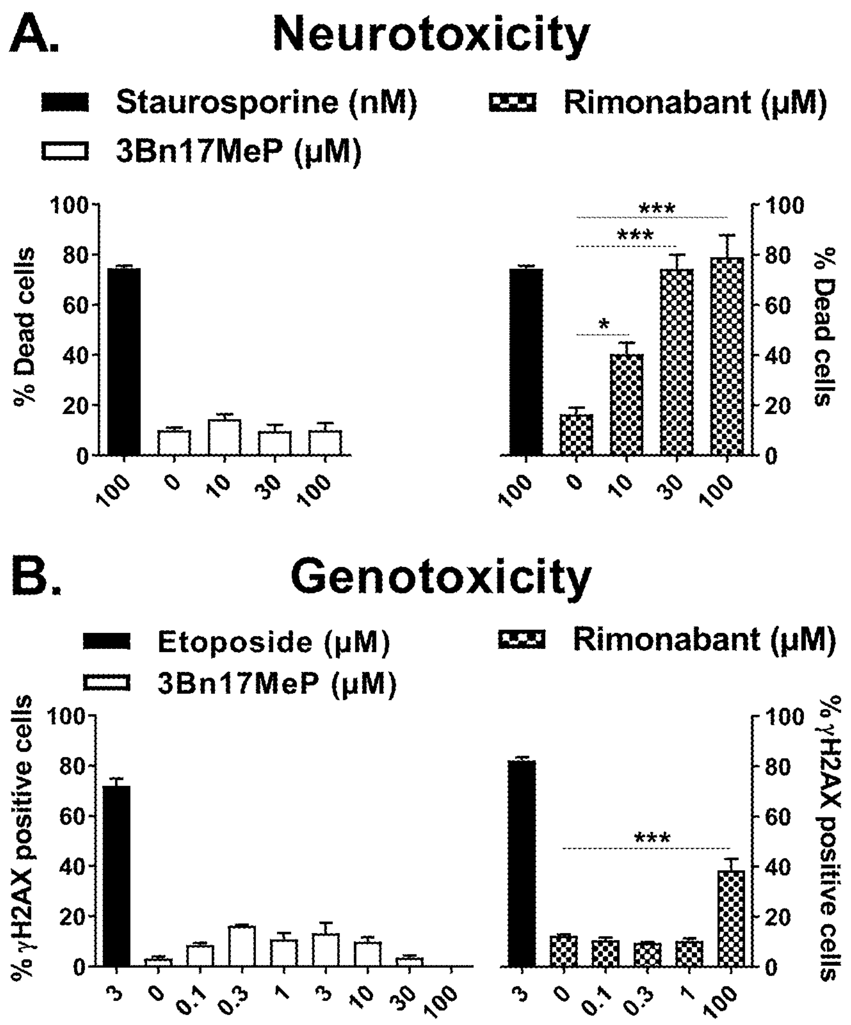
FIG. 13: Evaluation of neurotoxicity and genotoxicity of 3Bn17MeP and of rimonabant in vitro.
Figure 14:
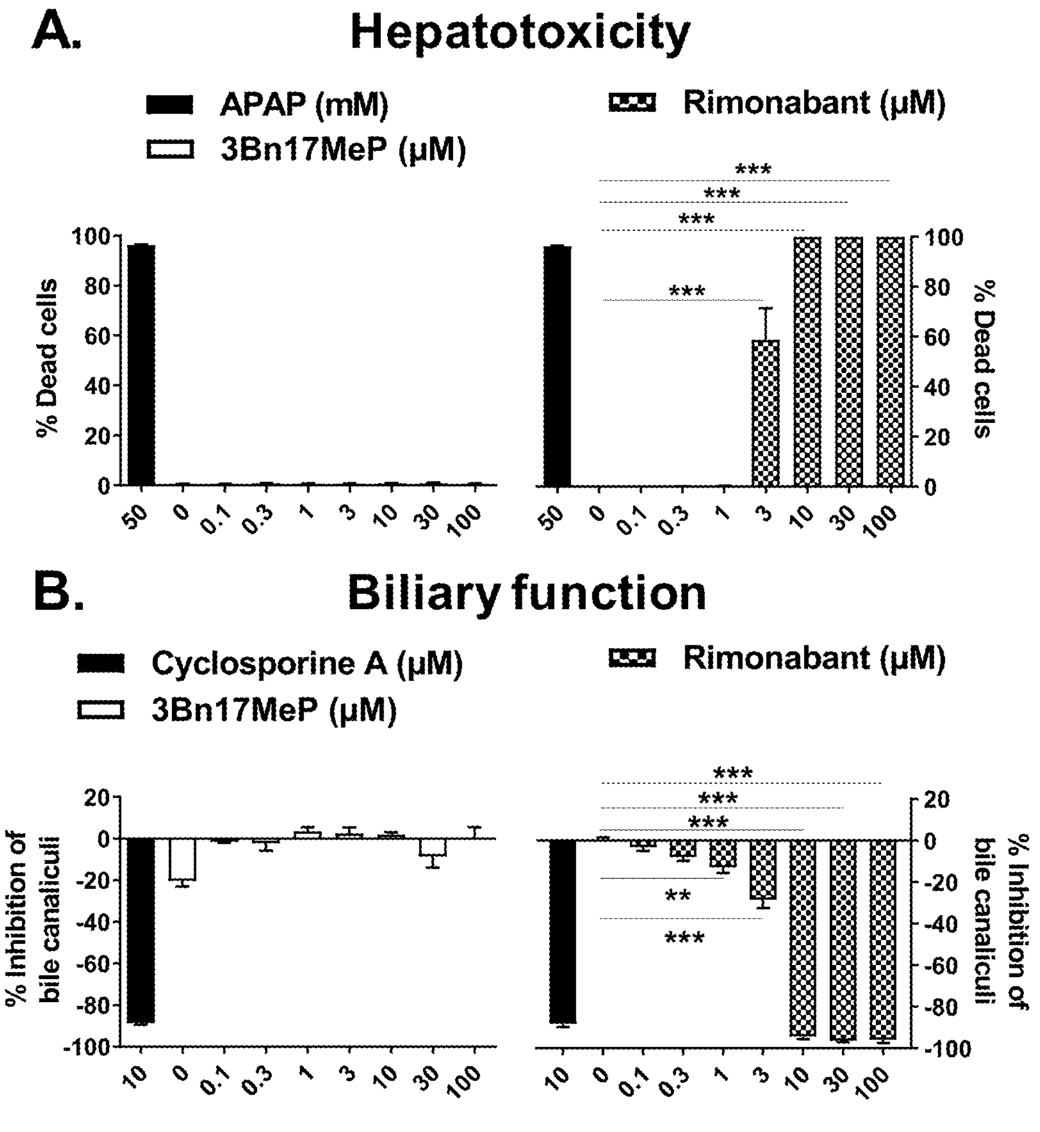
FIG. 14: Evaluation of hepatotoxicity of 3Bn17MeP and of rimonabant in vitro.

In contrast, rimonabant showed significant neurotoxicity from 10 μM and induced 80% of neural cell death from 30 μM (FIG. 13A). Rimonabant showed genotoxicity as it induced DNA damage at 100 μM (FIG. 13B). Rimonabant showed hepatotoxic effect as from 10 μM it induced 100% of hepatocyte death and suppressed bile canaliculi (FIG. 14A-B). For 3Bn17MeP, the maximum dose tested (100 μM) is 2000 times higher than the $ID_{100}$ of 3Bn17MeP to inhibit THC-induced decrease in cellular respiration (50 nM) in HEK-293 transfected with the human CB1 receptors (FIG. 5A).

Example 5b

In Vivo Safety of 3Bn17MeP

This study (CERB, France) aimed to evaluate in vivo effect of the 3Bn17MeP in Sprague-Dawley rats following dosing with 3Bn17MeP administered by the oral route once a day for 7 days.

Material and Methods

Rats (5 males, 5 females) received a fixed dose of 3Bn17MeP (20 mg/kg in 10 ml/kg of corn oil) once a day per os for 7 days.

Morbidity/mortality checks were performed twice daily. Clinical observations were performed before the first dosing and then daily. Functional and neurobehavioral tests were performed before the first dosing and on the last day of treatment. Body weight was recorded on Day-1, Day-3, Day-5 and Day-7. Food consumption was measured weekly.

Blood samples for haematology parameters and clinical chemistry analysis were collected on the day of necropsy (Day-8).

Blood samples for plasma drug analysis were collected after the last treatment, at 5 and 24 hours post-dose. Quantification was done by LC/MS-MS chromatography.

Animals were sacrificed on Day-8. Selected organs were weighed, fixed, preserved at necropsy and examined histopathologically.

Results

The only minor changes were seen in haematology and blood chemistry. In haematology, there was a tendency to a lower white blood cell counts in males and females and a slight tendency to a lower red blood cell counts in males. In blood chemistry, there was a tendency to lower total protein level and a higher triglyceride level. In females, there was a tendency to a lower triglyceride level. But these changes were not associated with any histopathological changes.

On Day-7, 5 hours after the last treatment, the mean plasma concentration of 3Bn17MeP was 4652.4 ng/ml. 24 hours after treatment, mean plasma concentration decreased to 973.8 ng/ml. These results showed that 3Bn17MeP was absorbed and that 24 hours after the last administration, it was not fully eliminated.

As a comparison, the mean plasma concentration measured in mice after one month of 3Bn17MeP administration in drinking water at a concentration reversing long-term memory impairments associated with ageing (example 7) and with Down syndrome (example 4) was 1.3 ng/ml. The ratio between this concentration and plasma concentration of 3Bn17MeP measured 5 hours after the last administration in this toxicity study (4652.4 ng/ml) revealed a high safety window that was >3500.

Conclusion

Under the experimental conditions adopted, 3Bn17MeP orally administered over 7 consecutive days did not induce any sign of toxicity at the dose of 20 mg/kg/day in the Sprague-Dawley rats. Consequently, after repeated treatment at a single dose, the maximum tolerated dose (MTD) is considered higher than 20 mg/kg/day.

Ratio between plasma concentration measured during in safety test and efficacy experiment show a high safety window that was >3500.

REFERENCES

Arnone, M., Maruani, J., Chaperon, F., Thiébot, M. H., Poncelet, M., Soubrié, P., and Le Fur, G. (1997). Selective inhibition of sucrose and ethanol intake by SR 141716, an antagonist of central cannabinoid (CB1) receptors. Psychopharmacology (Berl.) 132, 104-106.

Bellocchio, L., Soria-Gómez, E., Quarta, C., Metna-Laurent, M., Cardinal, P., Binder, E., Cannich, A., Delamarre, A., Häring, M., Martín-Fontecha, M., et al. (2013). Activation of the sympathetic nervous system mediates hypophagic and anxiety-like effects of $CB_1$ receptor blockade. Proc. Natl. Acad. Sci. U.S.A. 110, 4786-4791.

Beringer, P. (2011). Remington: the science and practice of pharmacy. (Philadelphia; London: Lippincott Williams & Wilkins).

Berry-Kravis, E., Hessl, D., Abbeduto, L., Reiss, A. L., Beckel-Mitchener, A., and Urv, T. K. (2013). Outcome Measures for Clinical Trials in Fragile X Syndrome: Journal of Developmental & Behavioral Pediatrics 34, 508-522.

Beyer, C. E., Dwyer, J. M., Piesla, M. J., Platt, B. J., Shen, R., Rahman, Z., Chan, K., Manners, M. T., Samad, T. A., Kennedy, J. D., et al. (2010). Depression-like phenotype following chronic CB1 receptor antagonism. Neurobiol. Dis. 39, 148-155.

Breton, M.-C., Turgeon, M., Tremblay, É., Gosselin, C., Institut national d'excellence en santé et en services sociaux (Québec), and Bibliothèque numérique canadienne (Firme) (2015). Traitement pharmacologique de la maladie d'Alzheimer et des maladies apparentées: rapport d'évaluation des technologies de la santé.

Burckhardt, C. S., and Anderson, K. L. (2003). The Quality of Life Scale (QOLS): reliability, validity, and utilization. Health Qual Life Outcomes 1, 60.

Busquets-Garcia, A., Gomis-González, M., Guegan, T., Agustín-Pavón, C., Pastor, A., Mato, S., Pérez-Samartín, A., Matute, C., de la Torre, R., Dierssen, M., et al. (2013). Targeting the endocannabinoid system in the treatment of fragile X syndrome. Nature Medicine 19, 603-607.

Carai, M. A. M., Colombo, G., Maccioni, P., and Gessa, G. L. (2006). Efficacy of rimonabant and other cannabinoid CB1 receptor antagonists in reducing food intake and body weight: preclinical and clinical data. CNS Drug Rev 12, 91-99.

Chang, K. T., Ro, H., Wang, W., and Min, K.-T. (2013). Meeting at the crossroads: common mechanisms in Fragile X and Down syndrome. Trends Neurosci. 36, 685-694.

Edgin, J. O., Mason, G. M., Spanò), G., Fernández, A., and Nadel, L. (2012). Human and mouse model cognitive phenotypes in Down syndrome: implications for assessment. Prog. Brain Res. 197,123-151.

Ennaceur, A. (2010). One-trial object recognition in rats and mice: methodological and theoretical issues. Behav. Brain Res. 215,244-254.

Esbensen, A. J., Hooper, S. R., Fidler, D., Hartley, S. L., Edgin, J., d'Ardhuy, X. L., Capone, G., Conners, F. A., Mervis, C. B., Abbeduto, L., et al. (2017). Outcome Measures for Clinical Trials in Down Syndrome. American Journal on Intellectual and Developmental Disabilities 122, 247-281.

Etchamendy, N., Konishi, K., Pike, G. B., Marighetto, A., and Bohbot, V. D. (2012). Evidence for a virtual human analog of a rodent relational memory task: A study of aging and fMRI in young adults. Hippocampus 22, 869-880.

Gardiner, K. J. (2015). Pharmacological approaches to improving cognitive function in Down syndrome: current status and considerations. Drug Des Devel Ther 9,103-125.

Grieco, J., Pulsifer, M., Seligsohn, K., Skotko, B., and Schwartz, A. (2015). Down syndrome: Cognitive and behavioral functioning across the lifespan. American Journal of Medical Genetics Part C: Seminars in Medical Genetics 169,135-149.

Hanney, M., Prasher, V., Williams, N., Jones, E. L., Aarsland, D., Corbett, A., Lawrence, D., Yu, L.-M., Tyrer, S., Francis, P. T., et al. (2012). Memantine for dementia in adults older than 40 years with Down's syndrome (MEADOWS): a randomised, double-blind, placebo-controlled trial. The Lancet 379,528-536.

Hessl, D., Sansone, S. M., Berry-Kravis, E., Riley, K., Widaman, K. F., Abbeduto, L., Schneider, A., Coleman, J., Oaklander, D., Rhodes, K. C., et al. (2016). The NIH Toolbox Cognitive Battery for intellectual disabilities: three preliminary studies and future directions. Journal of Neurodevelopmental Disorders 8.

Hunter, J., Rivero-Arias, O., Angelov, A., Kim, E., Fotheringham, I., and Leal, J. (2014). Epidemiology of fragile X syndrome: a systematic review and meta-analysis. Am. J. Med. Genet. A 164A, 1648-1658.

Kazdoba, T. M., Leach, P. T., Silverman, J. L., and Crawley, J. N. (2014). Modeling fragile X syndrome in the Fmr1 knockout mouse. Intractable Rare Dis Res 3,118-133.

Kishnani, P. S., Heller, J. H., Spiridigliozzi, G. A., Lott, I., Escobar, L., Richardson, S., Zhang, R., and McRae, T. (2010). Donepezil for treatment of cognitive dysfunction in children with Down syndrome aged 10-17. Am. J. Med. Genet. A 152A, 3028-3035.

Kumin, L., and Schoenbrodt, L. (2016). Employment in Adults with Down Syndrome in the United States: Results from a National Survey. Journal of Applied Research in Intellectual Disabilities 29,330-345.

Laprairie, R. B., Bagher, A. M., Kelly, M. E .M., Dupré, D. J., and Denovan-Wright, E. M. (2014). Type 1 cannabinoid receptor ligands display functional selectivity in a cell culture model of striatal medium spiny projection neurons. J. Biol. Chem. 289,24845-24862.

Marighetto, A., Brayda-Bruno, L., and Etchamendy, N. (2012). Studying the impact of aging on memory systems: contribution of two behavioral models in the mouse. Curr Top Behav Neurosci 10,67-89.

Moreira, F. A., Grieb, M., and Lutz, B. (2009). Central side-effects of therapies based on CB1 cannabinoid receptor agonists and antagonists: focus on anxiety and depression. Best Practice & Research Clinical Endocrinology & Metabolism 23,133-144.

Overstreet, D. H. (2012). Modeling depression in animal models. Methods Mol. Biol. 829, 125-144.

Patel, S., and Hillard, C. J. (2006). Pharmacological evaluation of cannabinoid receptor ligands in a mouse model of anxiety: further evidence for an anxiolytic role for endogenous cannabinoid signaling. J. Pharmacol. Exp. Ther. 318, 304-311.

Rinaldi-Carmona, M., Calandra, B., Shire, D., Bouaboula, M., Oustric, D., Barth, F., Casellas, P., Ferrara, P., and Le Fur, G. (1996). Characterization of two cloned human CB1 cannabinoid receptor isoforms. J. Pharmacol. Exp. Ther. 278, 871-878.

Seely, K. A., Brents, L. K., Franks, L. N., Rajasekaran, M., Zimmerman, S. M., Fantegrossi, W. E., and Prather, P. L. (2012). AM-251 and rimonabant act as direct antagonists at mu-opioid receptors: Implications for opioid/cannabinoid interaction studies. Neuropharmacology 63, 905-915.

Sellami, A., Al Abed, A. S., Brayda-Bruno, L., Etchamendy, N., Valério, S., Oulé, M., Pantaléon, L., Lamothe, V., Potier, M., Bernard, K., et al. (2017). Temporal binding function of dorsal CA1 is critical for declarative memory formation. Proc. Natl. Acad. Sci. U.S.A. 114, 10262-10267.

Sheehan, B. (2012). Assessment scales in dementia. Ther Adv Neurol Disord 5, 349-358.

Shore, D. M., Baillie, G. L., Hurst, D. H., Navas, F., Seltzman, H. H., Marcu, J. P., Abood, M. E., Ross, R. A., and Reggio, P. H. (2014). Allosteric Modulation of a Cannabinoid G Protein-coupled Receptor: BINDING SITE ELUCIDATION AND RELATIONSHIP TO G PROTEIN SIGNALING. Journal of Biological Chemistry 289, 5828-5845.

Vallée, M., Vitiello, S., Bellocchio, L., Hébert-Chatelain, E., Monlezun, S., Martin-Garcia, E., Kasanetz, F., Baillie, G. L., Panin, F., Cathala, A., et al. (2014). Pregnenolone can protect the brain from cannabis intoxication. Science 343, 94-98.

Varni, J. W., Seid, M., and Kurtin, P. S. (2001). PedsQL 4.0: reliability and validity of the Pediatric Quality of Life Inventory version 4.0 generic core scales in healthy and patient populations. Med Care 39, 800-812.

Walf, A. A., and Frye, C. A. (2007). The use of the elevated plus maze as an assay of anxiety-related behavior in rodents. Nat Protoc 2, 322-328.

Zavatti, M., Carnevale, G., Benelli, A., and Zanoli, P. (2011). Effects of the cannabinoid antagonist SR 141716 on sexual and motor behaviour in receptive female rats. Clin. Exp. Pharmacol. Physiol. 38, 771-775.

Diagnostic and statistical manual of mental disorders: DSM-5 (2013, Washington, D.C: American Psychiatric Association).

Rapport d'évaluation des médicaments indiqués dans le traitement symptomatique de la maladie d'ALZHEIMER (2016). Commission de la Transparence. Haute Autorité de Santé.

Donepezil, galantamine, rivastigmine and memantine for the treatment of Alzheimer's disease (2011). Technology appraisal guidance. National Institute for Health and Care Excellence.

EPAR discussion. https://www.ema.europa.eu/documents/scientific-discussion/acomplia-epar-scientific-discussion_en.pdf

The invention claimed is:

1. A method of treating a cognitive disorder, comprising administering to a human subject with Down syndrome or Fragile X syndrome and in need thereof a therapeutically effective amount of a compound according to Formula (I):

Formula (I)

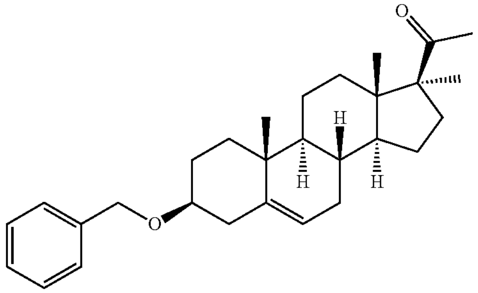

wherein the compound is administered to the subject at a dose of between 20 μg to 2 mg per day.

2. The method of claim 1, wherein the compound according to Formula (I) is administered to the subject by an oral route.

3. The method of claim 1, wherein the compound according to Formula (I) is administered to the subject by a parenteral route.

4. The method of claim 1, wherein the compound according to Formula (I) is administered to the subject by a route selected from the group consisting of an intravenous route, a subcutaneous route, an intranasal route, and an intramuscular route.

5. The method of claim 1, wherein the compound according to Formula (I) is administered to the subject at a dose of between 20 μg to 600 μg per day.

6. The method of claim 1, wherein the compound according to Formula (I) is administered to the subject at a dose of 100 μg per day.

7. The method of claim 1, wherein the compound according to Formula (I) is administered to the subject at a dose of 200 μg per day.

8. The method of claim 1, wherein the compound according to Formula (I) is administered to the subject at a dose of 600 μg per day.

9. The method of claim 5, wherein the compound according to Formula (I) is administered to the subject by an oral route.

10. The method of claim 6, wherein the compound according to Formula (I) is administered to the subject by an oral route.

11. The method of claim 7, wherein the compound according to Formula (I) is administered to the subject by an oral route.

12. The method of claim 8, wherein the compound according to Formula (I) is administered to the subject by an oral route.

* * * * *